(12) United States Patent
Sherman et al.

(10) Patent No.: US 12,201,501 B2
(45) Date of Patent: Jan. 21, 2025

(54) MEDICAL DRESSINGS WITH STIFFENING SYSTEMS

(71) Applicant: Solventum Intellectual Properties Company, Maplewood, MN (US)

(72) Inventors: Audrey A. Sherman, Woodbury, MN (US); Thomas R. J. Corrigan, St. Paul, MN (US); Dawn V. Muyres, Stillwater, MN (US); Silvia G. B. Guttmann, St. Paul, MN (US); Anne C. F. Gold, South St. Paul, MN (US); Michael R. Plumb, White Bear Lake, MN (US); Todd M. Fruchterman, West Lakeland, MN (US); Alex S. Plasencia, Shoreview, MN (US); Donald G. Peterson, Shoreview, MN (US); Krystal J. Scheibel, Minneapolis, MN (US); Zachary M. Ingram, Sioux, IA (US); Guido Hitschmann, Neuss (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 393 days.

(21) Appl. No.: 17/609,925

(22) PCT Filed: Jun. 1, 2020

(86) PCT No.: PCT/IB2020/055178
§ 371 (c)(1),
(2) Date: Nov. 9, 2021

(87) PCT Pub. No.: WO2020/245721
PCT Pub. Date: Dec. 10, 2020

(65) Prior Publication Data
US 2022/0226161 A1 Jul. 21, 2022

Related U.S. Application Data

(60) Provisional application No. 62/910,669, filed on Oct. 4, 2019, provisional application No. 62/857,501, filed on Jun. 5, 2019.

(51) Int. Cl.
*A61F 13/02* (2024.01)
*A61F 13/00* (2024.01)
*A61F 13/0246* (2024.01)

(52) U.S. Cl.
CPC ........ *A61F 13/023* (2013.01); *A61F 13/0246* (2013.01); *A61F 2013/00412* (2013.01)

(58) Field of Classification Search
CPC .... A61F 13/023; A61F 13/0246; A61F 13/02; A61F 13/00; A61F 13/00021;
(Continued)

(56) References Cited

U.S. PATENT DOCUMENTS

RE24,906 E 12/1960 Ulrich
3,389,824 A 6/1968 Berchtold
(Continued)

FOREIGN PATENT DOCUMENTS

CN 1257414 A 6/2000
CN 101785726 A 7/2010
(Continued)

OTHER PUBLICATIONS

International Search Report for PCT International Application No. PCT/IB2020/055178, mailed on Jul. 3, 2020, 6 pages.

*Primary Examiner* — Caitlin A Carreiro
(74) *Attorney, Agent, or Firm* — Mueting Raasch Group

(57) ABSTRACT

Medical dressings including stiffening systems fixedly attached to backing layers are described herein along with methods of using the medical dressings. The stiffening system is fixedly secured to the backing to limit flexing and
(Continued)

stretching of the backing layer. Typically, the medical dressing and stiffening system is applied over a medical device that is secured to skin. The stiffening system covers some of the medical device and also extends beyond the medical device. The stiffening system stabilizes the medical device over the skin.

18 Claims, 22 Drawing Sheets

(58) Field of Classification Search
CPC .. A61F 2013/00412; A61F 2013/00089; A61F 2013/00259; A61F 2013/00582
USPC .............................. 602/41–43, 52, 54, 58, 60
See application file for complete search history.

(56) References Cited

U.S. PATENT DOCUMENTS

| | | | |
|---|---|---|---|
| 3,389,827 A | | 6/1968 | Abere |
| 3,645,835 A | | 2/1972 | Hodgson |
| 4,112,213 A | | 9/1978 | Waldman |
| 4,310,509 A | | 1/1982 | Berglund |
| 4,323,557 A | | 4/1982 | Rosso |
| 4,472,480 A | | 9/1984 | Olson |
| 4,595,001 A | | 6/1986 | Potter |
| 4,737,410 A | | 4/1988 | Kantner |
| 5,088,483 A | | 2/1992 | Heinecke |
| 5,160,315 A | | 11/1992 | Heinecke |
| 5,264,218 A | * | 11/1993 | Rogozinski ............ A61L 15/42 |
| | | | 424/443 |
| 5,533,503 A | | 7/1996 | Doubek |
| 5,546,929 A | | 8/1996 | Muchin |
| D430,674 S | | 9/2000 | Dunshee |
| 6,479,724 B1 | | 11/2002 | Areskoug |
| D495,419 S | | 8/2004 | Dunshee |
| 6,893,655 B2 | | 5/2005 | Flanigan |
| 6,994,904 B2 | | 2/2006 | Joseph |
| 7,294,752 B1 | * | 11/2007 | Propp .................... A61M 25/02 |
| | | | 602/42 |
| 7,407,709 B2 | | 8/2008 | Zhou |
| 8,486,004 B1 | | 7/2013 | Propp |
| D690,425 S | | 9/2013 | Heinecke |
| 8,822,559 B2 | | 9/2014 | Zoller |
| 8,822,560 B2 | | 9/2014 | Seth |
| 9,359,529 B2 | | 6/2016 | Liu |
| 2004/0162512 A1 | * | 8/2004 | Liedtke .............. A61F 13/0259 |
| | | | 602/42 |
| 2008/0039759 A1 | | 2/2008 | Holm et al. |
| 2008/0071224 A1 | | 3/2008 | Forsyth |
| 2008/0132821 A1 | | 6/2008 | Propp et al. |
| 2011/0098621 A1 | * | 4/2011 | Fabo .................... A61F 13/023 |
| | | | 602/52 |
| 2011/0206924 A1 | | 8/2011 | Liu |
| 2014/0005607 A1 | * | 1/2014 | Elsamahy ............. A61F 13/023 |
| | | | 604/180 |
| 2015/0141949 A1 | | 5/2015 | Decabooter |
| 2016/0317699 A1 | * | 11/2016 | Dicosmo ................ A61L 15/26 |

FOREIGN PATENT DOCUMENTS

| | | |
|---|---|---|
| JP | 2006518259 A | 8/2006 |
| JP | 2010500124 | 4/2010 |
| WO | WO2007-028200 | 3/2007 |
| WO | WO2019-073326 | 4/2019 |
| WO | WO2020-136614 | 7/2020 |
| WO | WO2021-090136 | 5/2021 |

\* cited by examiner

MEDICAL DRESSINGS WITH STIFFENING SYSTEMS

CROSS REFERENCE TO RELATED APPLICATIONS

This application is a national stage filing under 35 U.S.C. 371 of PCT/IB2020/055178, filed Jun. 1, 2020, which claims the benefit of Provisional Application No. 62/910,669, filed Oct. 4, 2019, and Provisional Application No. 62/857,501, filed Jun. 5, 2019, the disclosure of which is incorporated by reference in its/their entirety herein.

TECHNICAL FIELD

Medical dressings including stiffening systems fixedly attached to backing layers are described herein along with methods of using the medical dressings.

BACKGROUND

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.) and OP-SITE™ (Smith & Nephew, Hull, England).

Thin polymeric films that are flexible and resilient are beneficial when used on skin that flexes, stretches, and retracts. However, for some applications, like when securing devices such as tubing, ports, and catheters, the high flexibility and resiliency of the thin polymeric film can allow or permit unwanted movement of the secured medical device. Therefore, medical dressings have been developed that further incorporate areas having secured to the thin polymeric film, stiffer, less conformable materials such as adhesives, films, or fabrics. For example, U.S. Pat. No. 5,088,483 discloses an adhesive composite dressing that includes a conformable backing and a permanent adhesive reinforcement around the periphery of the adhesive composite. One example of a commercially available medical dressing with a reinforcement layers is TEGADERM™ IV Advanced Dressing (3M Company, St. Paul Minn.).

In some instances, medical dressings are applied to a patient and remain in place for several days. When dressings are worn over time, the edge of the dressing can begin to peel away from the patient possibly resulting in contamination at the site or adhesive failure entirely. The use of less resilient materials to add stiffness and reduce flexibility in areas of the dressing can contribute to adhesive failure of the dressing on skin. When the skin flexes and stretches, but the less resilient material cannot flex and/or stretch, then the adhesive may be more likely to pull away from the skin.

SUMMARY

Medical dressings including stiffening systems fixedly attached to backing layers are described herein along with methods of using the medical dressings.

The backing layers used in medical dressings may be both elastic and provide a sufficiently impermeable barrier to the passage of liquids and at least some gases to protect a covered site from external contaminants. Elasticity allows the backing layer to expand, contract, stretch and recover as an underlying substrate, such as, e.g., skin, moves, and/or to conform to the shape of an underlying surface or article (for example, tubing, a catheter hub, etc.).

The materials used to form the backing layers may have a relatively low modulus of elasticity such that the backing layer exhibits elasticity. In contrast to the backing layers, the materials used to form the stiffening elements of stiffening systems of the medical dressings described herein may have a relatively high modulus of elasticity, resulting in the stiffening system elements exhibiting less elasticity than the backing layer. As a result, where the stiffening system of a medical dressing is fixedly attached to the backing layer (forming a stiffening system/backing layer composite), the stiffening system restrains the backing layer such that the stiffening system/backing layer composite exhibits an elasticity that is less than the elasticity of the backing layer alone.

The backing layers of medical dressings may have a relatively low flexural or bending modulus such that the backing layer itself exhibits relatively low resistance to bending. In contrast to the backing layers, the stiffening elements of stiffening systems of the medical dressings may have a relatively high flexural or bending modulus such that the stiffening system elements exhibit a higher resistance to bending than the backing layer. As a result, where the stiffening system of a medical dressing is fixedly attached to the backing layer (forming a stiffening system/backing layer composite), the stiffening system supports the backing layer such that the stiffening system/backing layer composite exhibits a higher flexural or bending modulus and, therefore, is less likely to bend, fold, droop, etc. when not supported by other components of a dressing delivery system.

The resistance provided to the backing layers by the stiffening systems fixedly attached to those backing layers may enhance the ability of the medical dressings described herein to maintain their shape in response to forces exerted on the backing layer. These forces may become concentrated where, for example, the medical dressing is applied over an object such as, for example, a catheter hub, tubing, etc. In the absence of a stiffening system, the backing layer alone may provide only limited restraint on the movement of such objects. The addition of a stiffening system may improve the ability of a medical dressing to restrain movement of such objects while maintaining desirable properties of the backing layers themselves. The stiffening system may improve the ability of a medical dressing to be accurately placed at a selected location without folding, drooping, or otherwise deforming undesirably.

The stiffening systems may control the elongation or stiffness of the backing layers in a prescribed way, which can improve long-term adhesion of the medical dressing over a wound and/or article. The stiffening system may control elongation of the backing in an unsupported area of the medical dressing, where the medical dressing spans between the skin and the medical device over free space.

In some embodiments, the stiffening system is radially symmetric such that elongation of the backing layer can be controlled around the geometric center of the stiffening system. In some embodiments, the stiffening system is biaxially symmetric such that elongation of the backing layer can be controlled around a stiffening axis of the stiffening system, while in still other embodiments, the stiffening system is axially symmetric to preferentially control elongation of the backing layer in one direction.

Although potential issues associated with the stretching of thin polymeric films used in medical dressings is known, approaches to addressing that issue often include adding one or more layers of materials to limit stretching of the thin polymeric films. Those additional layers may, however, prevent visualization of surface and/or articles located beneath those layers.

One or more embodiments of the stiffening systems of medical dressings described herein, include stiffening elements that are spaced apart such that substantial areas of the backing layer remain free of stiffening elements. Visualization through those substantial areas of the backing layer is unimpeded by the stiffening elements of stiffening systems. Further, one or more embodiments of stiffening systems of medical dressings may be constructed of materials that are substantially transparent such that visualization through the portions of the backing layer to which the stiffening elements are fixedly attached is not significantly degraded as compared to areas where stiffening elements are not fixedly attached.

In other embodiments of stiffening systems, all or portions of the stiffening systems may provide a visual contrast with the surrounding backing layers (for example, all or portions of the stiffening elements may be opaque and/or exhibit a selected color or colors). In such embodiments, the contrast between the stiffening systems and surrounding backing layers may be useful during application of a medical dressing over a selected area, wound, article, etc.

Including additional layers to a backing layer to provide mechanical support may reduce the moisture vapor permeability of the thin polymeric films and add thickness to the medical dressing. One or more embodiments, the stiffening elements that are spaced apart such that substantial areas of the backing layer remain free of stiffening elements. Moisture vapor permeability through those substantial areas of the backing layer is unimpeded by the stiffening elements of stiffening systems.

In still other embodiment, the additional layers if brought to the edge of the medical dressing may concentrate forces along the stiffer edges of those additional layers, and that force concentration may be detrimental to long-term adhesion of the medical dressing over a wound and/or article. One or more embodiments of stiffening systems do not form structures that concentrate forces proximate a border of the medical dressing and, as such, may not be detrimental to long-term adhesion of the medical dressing over a wound and/or article. In one embodiment, the stiffening system is near but not at the perimeter edge of the medical dressing. Instead, the stiffening system is recessed from the perimeter edge, such that the adhesive on the underlying surface of the medical dressing securely holds the stiffening system to the underlying surface.

In one embodiment, the medical dressing with the stiffening system is arrange over a medical device. A portion of the stiffening system overlies the medical device, a portion of the stiffening system extends from the medical device to be adjacent the underlying surface. The adhesive on the medical dressing securely fixes the medical dressing and stiffening system to the underlying surface. In this embodiment, the stiffening system functions like a load beam limiting stretching of the backing layer and distributing any external forces. The stiffening system securely holds the medical device to the underling surface.

In one embodiment, the medical dressing includes: a backing layer comprising a first major surface, a second major surface, and a perimeter defining a backing area on each of the first and second major surfaces; adhesive on at least a portion of the first major surface of the backing layer, wherein the backing layer and the adhesive form a substantially contact transparent backing layer/adhesive composite; and a stiffening system fixedly attached to the backing layer, wherein the stiffening system is contained within a selected region of the backing layer, the selected region defining a region perimeter; wherein the stiffening system comprises a plurality of elongated stiffening elements contained within the region perimeter of the selected region, wherein each stiffening element of the plurality of stiffening elements extends along a length from a first end to a second end, wherein the first end of each stiffening element of plurality of stiffening elements is located closer to a center of the selected region than the second end, and wherein the second end of each stiffening element of plurality of stiffening elements is located closer to the region perimeter than the first end, and further wherein the selected region not occupied by the stiffening system is, optionally, substantially contact transparent.

In one embodiment, the medical dressing includes: a backing layer comprising a first major surface, a second major surface, and a perimeter defining a geometric center of the backing layer; adhesive on at least a portion of the first major surface of the backing layer, wherein the backing layer and the adhesive provide a contact transparent adhesive composite; and a stiffening system fixedly attached to the backing layer, the stiffening system comprising an array of a plurality of stiffening elements. Each stiffening element of the plurality of stiffening elements comprises: a first end and a second end located distal from the first end, wherein the first end is located closer to the geometric center of the backing layer than the second end, and wherein the second end is located closer to the perimeter of the backing layer than the first end; a length defining a stiffening axis extending from the first end to the second end of the stiffening element, wherein a width of the stiffening element as measured transverse to the length that is less than the length; wherein the stiffening axis extends away from the first end and towards the perimeter of the backing layer.

In one embodiment, the medical dressing includes: a backing layer comprising a first major surface, a second major surface, and a perimeter defining a geometric center of the backing layer; adhesive on at least a portion of the first major surface of the backing layer, wherein the backing layer and the adhesive provide a contact transparent adhesive composite; and a stiffening system fixedly attached to the backing layer, wherein the stiffening system comprises a plurality of nested stiffening elements positioned on the backing layer, wherein each stiffening element of the plurality of nested stiffening elements defines a ring having a radial width less than a ring length, wherein the radial width is defined along a radial axis extending outwardly from a center of the ring and the ring length is defined along a line following a center of the radial width.

In one embodiment, the medical dressing includes: a backing layer comprising a first major surface, a second major surface, and a perimeter defining a geometric center of the backing layer; adhesive on at least a portion of the first major surface of the backing layer, wherein the backing layer and the adhesive provide a contact transparent adhesive composite; and a stiffening system fixedly attached to the backing layer, wherein the stiffening system defines a stiffening axis extending across the backing layer in a selected direction, the stiffening system comprising a plurality of stiffening elements on the backing layer. Each stiffening element of the plurality of stiffening elements comprises: a first end and a second end defining a length along a longitudinal axis extending through the first and second ends and a width measure transverse to the longitudinal axis; wherein the first end and the second end are spaced inwardly from the perimeter of the backing layer; and wherein the longitudinal axis is aligned with the stiffening axis of the stiffening system.

In one embodiment, the medical dressing includes: a backing layer comprising a first major surface, a second major surface, and a perimeter defining a backing area on each of the first and second major surfaces; adhesive on at least a portion of the first major surface of the backing layer, wherein the backing layer and the adhesive form a substantially contact transparent backing layer/adhesive composite; and a stiffening system fixedly attached to the backing layer, wherein the stiffening system is contained within a selected region of the backing layer, the selected region defining a region perimeter; wherein the stiffening system comprises a plurality of elongated stiffening elements contained within the region perimeter of the selected region, wherein each stiffening element of the plurality of stiffening elements extends along a length from a first end to a second end, wherein the first end of each stiffening element of plurality of stiffening elements is located closer to a center of the selected region than the second end, and wherein the second end of each stiffening element of plurality of stiffening elements is located closer to the region perimeter than the first end, and further wherein the selected region not occupied by the stiffening system is substantially contact transparent.

In one embodiment, the medical dressing includes: a backing layer comprising a first major surface, a second major surface, and a perimeter; adhesive on at least a portion of the first major surface of the backing layer; and a stiffening system fixedly attached to the backing layer, wherein the stiffening system is contained within a selected interior region of the backing layer, the selected interior region being spaced inward from the perimeter of the backing layer. The stiffening system comprises a plurality of stiffening elements contained within the selected interior region, wherein the plurality of stiffening elements comprises a plurality of nested stiffening elements, wherein each stiffening element of the plurality of nested stiffening elements defines a ring located within the selected interior region and further wherein an outermost stiffening element of the plurality of nested stiffening elements is spaced inward from the backing layer perimeter and is completely surrounded by the backing layer.

In one embodiment the medical dressing includes: a backing layer comprising a first major surface, a second major surface, and a perimeter; adhesive on at least a portion of the first major surface of the backing layer; and a stiffening system fixedly attached to the backing layer, wherein the stiffening system is contained within a selected interior region of the backing layer, the selected interior region being spaced inward from the perimeter of the backing layer. The stiffening system defines a stiffening axis extending across the selected interior region in a selected direction, the stiffening system comprising a plurality of stiffening elements, wherein each stiffening element of the plurality of stiffening elements comprises: a first end and a second end defining a length along a longitudinal axis extending through the first and second ends and a width measure transverse to the longitudinal axis; wherein the first end and the second end are located within the selected interior region and spaced inwardly from the perimeter of the backing layer such that the first and second ends are completely surrounded by the backing layer; and wherein the longitudinal axis is aligned with the stiffening axis of the stiffening system.

In one embodiment, the medical dressing includes: a backing layer comprising a first major surface, a second major surface, and a perimeter surrounding a central region; adhesive on at least a portion of the first major surface of the backing layer; and a stiffening system fixedly attached to the backing layer; wherein the stiffening system comprising a plurality of stiffening elements, wherein each stiffening element of the plurality of stiffening elements comprises a first end at the central region and a second end located distal from the first end near the perimeter, but not at the perimeter; wherein each stiffening element second end is surrounded by the backing layer containing adhesive.

In one embodiment, the medical dressing for covering a device on a substrate includes: a backing layer comprising a first major surface, a second major surface, and a perimeter surrounding a central region; adhesive on at least a portion of the first major surface of the backing layer; and a stiffening system fixedly attached to the backing layer; wherein the stiffening system comprising a plurality of stiffening elements, wherein each stiffening element of the plurality of stiffening elements comprises a first end at the central region and a second end located distal from the first end near the perimeter, but not at the perimeter; wherein each stiffening element second end is surrounded by the backing layer containing adhesive, wherein at least a portion of the stiffening system is applied over the device and the second end of the stiffening elements are applied to the substrate.

In one embodiment, the medical dressing includes: a backing layer comprising a first major surface, a second major surface, and a perimeter surrounding a central region; adhesive on at least a portion of the first major surface of the backing layer; and a stiffening system on the backing layer; wherein the stiffening system comprises: a first ring-shaped stiffening element located within the central region; a second ring-shaped stiffening element surrounding the first ring-shaped stiffening element, the second ring-shaped stiffening element spaced inwardly from the perimeter of the backing layer, wherein each ring-shaped stiffening element is surrounded by the backing layer containing adhesive.

In one embodiment, the medical dressing for covering a device over a substrate includes: a backing layer comprising a first major surface, a second major surface, and a perimeter surrounding a central region; adhesive on at least a portion of the first major surface of the backing layer; and a stiffening system on the backing layer. The stiffening system comprises: a first radially extending stiffening element at the central region; a second radially extending stiffening element near the perimeter, but not at the perimeter; wherein each stiffening element is surrounded by the backing layer containing adhesive; wherein at least a portion of the stiffening system is applied over the device and the second stiffening element is applied to the substrate.

In one embodiment, the medical dressing includes: a backing layer comprising a first major surface, a second major surface, and a perimeter; adhesive on at least a portion of the first major surface of the backing layer; and a stiffening system fixedly attached to the backing layer, wherein the stiffening system comprises any one or more features of stiffening systems described herein.

In one embodiment, a method of improving patency of blood vessels proximate a catheter insertion site includes: positioning a medical dressing comprising a stiffening system over a catheter insertion site; and adhesively attaching the medical dressing to skin proximate the insertion site such that a pair of stiffening elements of the stiffening system are located on opposite sides of the catheter insertion site.

If used herein, the term "substantially" has the same meaning as "significantly," and can be understood to modify the term that follows by at least about 75%, at least about 90%, at least about 95%, or at least about 98%. The term "not substantially" as used here has the same meaning as "not significantly," and can be understood to have the inverse meaning of "substantially," i.e., modifying the term that follows by not more than 25%, not more than 10%, not more than 5%, or not more than 2%.

Numeric values used herein include normal variations in measurements as expected by persons skilled in the art and should be understood to have the same meaning as "approximately" and to cover a typical margin of error, such as ±5% of the stated value.

Terms such as "a," "an," and "the" are not intended to refer to only a singular entity but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

BRIEF DESCRIPTION OF DRAWINGS

FIGS. 30A and 3B depict embodiments of a medical dressing including a stiffening system.

While the above-identified drawings and figures (which may or may not be drawn to scale) set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope of this invention.

DESCRIPTION

Figure 1:
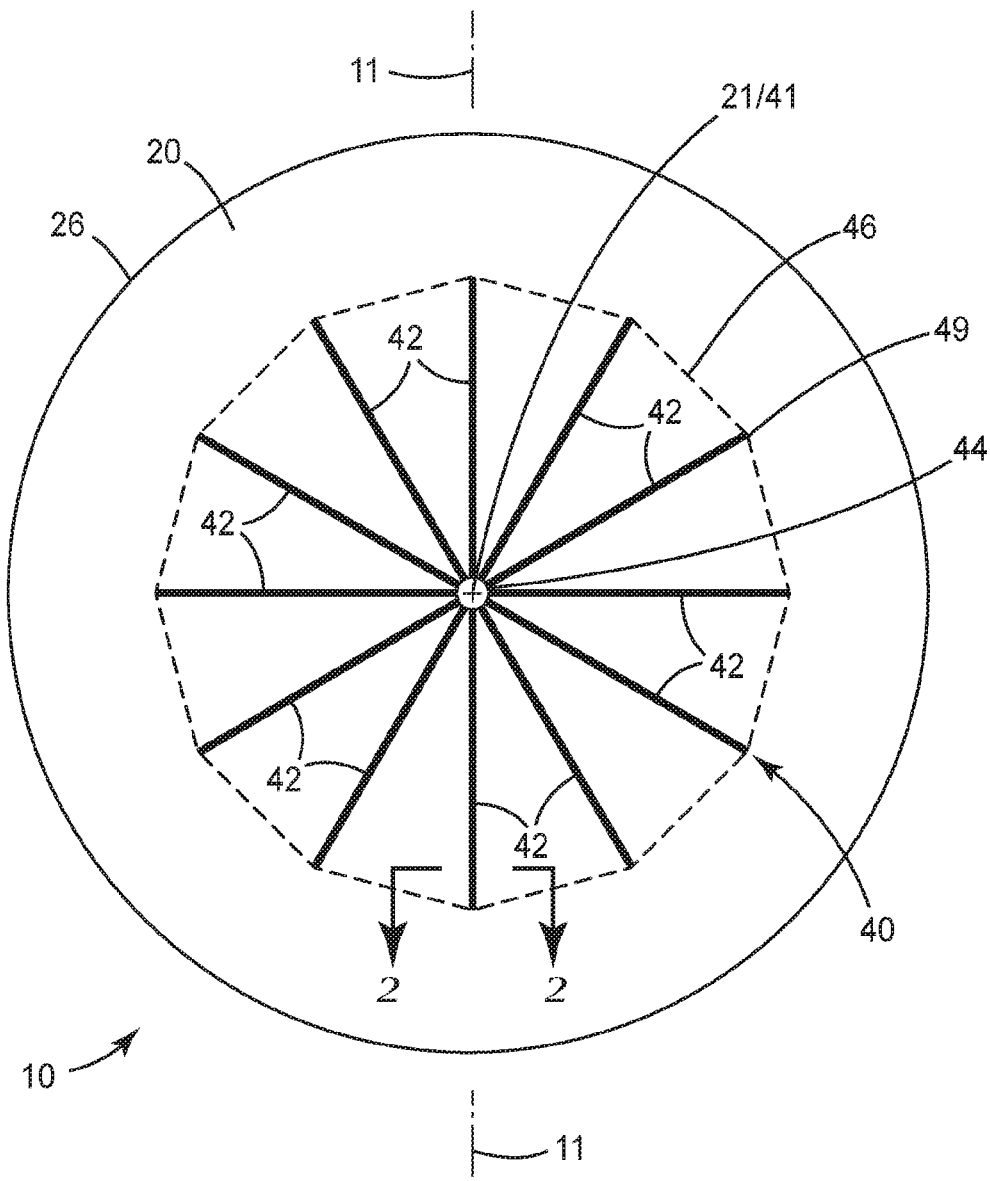
FIG. 1 is a top view of one embodiment of a medical dressing including a stiffening system on a backing layer.
Figure 2A:
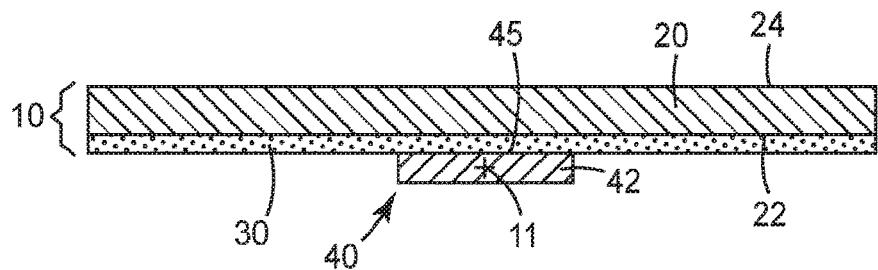
FIG. 2A is an enlarged cross-sectional view of a portion of the medical dressing of FIG. 1 taken along line 2-2 in FIG. 1.

FIG. 1 depicts one major surface of one embodiment of a medical dressing 10, while FIG. 2A is an enlarged cross-sectional view of a portion of the medical dressing 10 taken along line 2-2 in FIG. 1. A medical dressing such as medical dressing 10 may be used to cover a wound, selected area of the skin of a patient, a medical article positioned above the skin of a patient, etc.

The medical dressing 10 includes a backing layer 20 having a first major surface 22 and a second major surface 24. The backing layer 20 also defines a perimeter 26 at its outer edges, with the perimeter 26 of the backing layer 20 also typically defining the perimeter of the medical dressing 10. In addition to defining a perimeter 26, the backing layer 20 also defines a geometric center 21 of the first and second major surfaces 22 and 24 of the backing layer 20 (where the geometric center is determined when the medical dressing 10 is in a flat or planar configuration).

The backing layer 20 may be in the form of a thin polymeric film. Backing layers that may be used in one or more embodiments are described in the backing layer section below.

Medical dressing 10 also includes adhesive 30 on at least a portion of the first major surface 22 of the backing layer 20. Typically, the first major surface 22 of the backing layer 20 carrying adhesive 30 may be referred to as the skin-facing surface of the medical dressing when the adhesive 30 is selected for adhesion to skin. Examples of adhesive are discussed in the adhesive section provided below. Together, the backing layer 20 and adhesive 30 may, in one or more embodiments, provide a contact transparent adhesive composite suitable for attachment to skin.

The medical dressing 10 includes a stiffening system. One embodiment of a stiffening system 40 is also included as a part of medical dressing 10. The stiffening system can comprise one or more stiffening elements 42.

A cross-sectional view of a portion of stiffening system 40 is in FIG. 2A. Each stiffening element 42 of stiffening system 40 can be fixedly attached to the first major surface 22 of the backing layer 20. The stiffening system includes an array of a plurality of stiffening elements 42, each of which is fixedly attached to the backing layer 20 as shown in FIG. 1. Further, in the embodiment of FIG. 2A, each stiffening element 42 is fixedly attached to the backing layer 20 using adhesive 30 positioned between each of the stiffening elements 42 and the first major surface 22 of the backing layer 20.

Figure 2B:
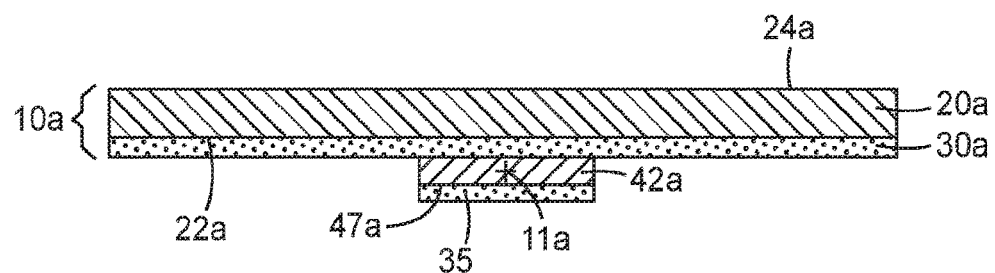
FIG. 2B is an enlarged cross-sectional view of portion of an embodiment of medical dressing in FIG. 2A.

FIG. 2B is a cross-sectional view of a portion of medical dressings depicting a construction to that depicted in FIG. 2A. Medical dressing 10a is essentially similar to medical dressing 10 shown in FIG. 2A. Specifically, medical dressing 10a includes a backing layer 20a having a first major surface 22a and a second major surface 24a. An adhesive 30a is disposed on at least a portion of the first major surface 22a of the backing layer 20a. In one or more embodiments, the backing layer 20a may be in the form of a thin polymeric film. In an exemplary aspect, the polymer film has a low modulus of elasticity yielding a highly conformable and elastic dressing. Together, the backing layer 20a and adhesive 30a may provide a contact transparent adhesive composite suitable for attachment to skin creating a viewing field that enables visualization of the skin, tissue, or medical device disposed beneath at least a portion of the medical dressing.

It can be desirable to control the elasticity of the backing in certain regions, such as when the medical dressing is placed over a medical device and the elastic nature of the backing may allow the medical device to shift or move. A stiffening system may be incorporated into part of medical dressing to provide support for the medical device. For example, a stiffening system may be fixedly attached to the first major surface 22a of the backing layer 20a by adhesive 30a. The stiffening system includes an array of stiffening elements, such as stiffening element 42a in FIG. 2B. Stiffening element 42a includes an adhesive layer 35 disposed on surface 47a such that at least a portion of the stiffening element may be adhered to skin, tissue, or medical device disposed beneath at least a portion of the medical dressing.

Figure 3A:
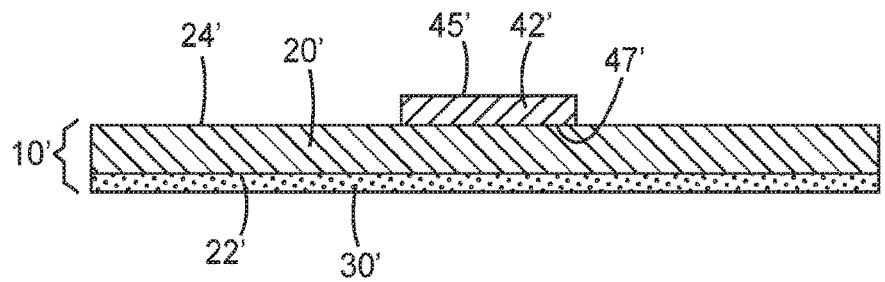
FIGS. 3A and 3B are enlarged cross-sectional views of portions of embodiments of medical dressings in FIG. 2A.
Figure 3B:
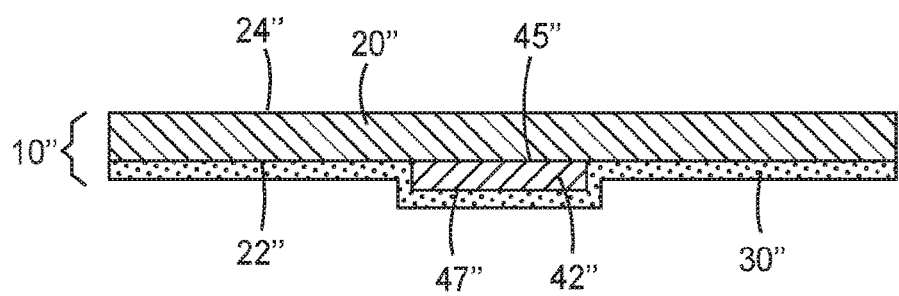

Two potentially constructions used to fixedly attach stiffening elements of a stiffening system to a backing layer of a medical dressing are depicted in FIGS. 3A-3B. With reference to FIG. 3A, the medical dressing 10' includes a backing layer 20' having a first major surface 22' and a second major surface 24'. Adhesive 30' is provided on the first major surface 22' of the backing layer 20'. Unlike stiffening element 42 of medical dressing 10 as described above, stiffening element 42' of medical dressing 10' is fixedly attached to the second major surface 24' of the backing layer 20', with the second major surface 47' of stiffening element 42' facing the second major surface 24' of backing layer 20', while first major surface 45' of stiffening element 42' faces away from the backing layer 20'. Stiffening elements 42' may be fixedly attached to the backing layer 20' by any suitable technique or combination of techniques including, but not limited to, adhesives (for example, pressure sensitive adhesives, heat-activated laminating adhesives, etc.), glues, chemical welding, thermal welding, ultrasonic welding, etc.

As used herein, "fixedly attached" (and variations thereof) describes an attachment between the stiffening system and the backing layer that would result in permanent (i.e., plastic) deformation of one or both of the backing layer and the stiffening system upon separation of stiffening system from the backing layer.

With reference to FIG. 3B, the medical dressing 10" includes a backing layer 20" having a first major surface 22" and a second major surface 24". Adhesive 30" is provided on the first major surface 22" of the backing layer 20". Stiffening elements 42" are fixedly attached to the first major surface 22" of backing layer 20", with the first major surface 45" of element 42" facing the first major surface 22" of backing layer 20" and second major surface 47" of stiffening element 42" facing away from backing layer 20". Unlike, however, stiffening elements 42 of medical dressing 10 as described above, adhesive 30" is not used to attach stiffening elements 42" to the first major surface 22" backing layer 20". Rather, stiffening elements 42" may be fixedly attached to the backing layer 20" by any suitable technique or combination of techniques including, but not limited to, adhesives (other than adhesive 30"), chemical welding, thermal welding, ultrasonic welding, etc.

The stiffening system can be a separate film or layer of material applied to the backing as shown in FIGS. 2B, 3A, and 3B. In some embodiments, the stiffening system can be a flowable or liquid material coated, extruded, printed, microreplicated, or otherwise applied onto the backing. Then, the material is cured by drying, crosslinking to harden forming the stiffening system. Crosslinking can be from catalyst curing or radiation curing, such as e-beam curing. Upon curing, these materials are stiffer, less elastic then the backing layer. The flowable or liquid material could be applied over substantially the entire backing and the curing could be targeted to areas of the backing. In other embodiment, the flowable or liquid material could be applied to discrete areas of the backing. Similar to FIGS. 2B, 3A, and 3B coated materials could be applied on either surface of the backing.

Referring again to FIG. 1, stiffening system 40 as depicted in connection a medical dressing 10 including stiffening elements 42 can be characterized as defining a stiffening system perimeter 46, where the stiffening system perimeter 46 is determined by boundary lines extending between the outermost ends of each of the stiffening elements 42, where the outermost ends of the stiffening elements 42 are defined as those ends located furthest away from the geometric center 21 of the backing layer 20. In the embodiment in FIG. 1, the stiffening system perimeter 46 is defined by the broken lines extending between the outermost ends of stiffening elements 42.

The stiffening system perimeter 46 can be used to define a stiffening system geometric center 41 (where the geometric center of the stiffening system is determined when the medical dressing 10 is in a flat or planar configuration). In the embodiment of medical dressing 10, the geometric center 21 of the backing layer 20 and the geometric center 41 of the stiffening system are coincident.

In one embodiments, the geometric center 21 of the backing layer 20 and the geometric center 41 of the stiffening system may or may not be coincident. In one embodiment, the geometric center of a backing layer may simply be located within the stiffening system perimeter. The stiffening system geometric center may merely be proximate the geometric center of the backing layer on which the stiffening system is located.

The stiffening system perimeter 46 may define a stiffening system area on the first major surface 22 and/or second major surface 24 of the backing layer 20. The stiffening system may be described as occupying or being contained within a selected region of the backing layer 20 with the selected region being defined by the stiffening system perimeter 46 and being referred to as a region perimeter 46. Similar descriptions may be applied to any medical dressing described herein, in other words, the stiffening system perimeter of any stiffening system may be described as a selected region on the backing layer having a region perimeter, with the stiffening system being contained within the selected region.

In one embodiment, the stiffening system area defined by a stiffening system perimeter may occupy 50% or more, 60% or more, 70% or more, 80% or more, 90% or more, 95% or more, or even all of a backing area defined by the first major surface and/or second major surface of the backing layer. Providing a stiffening system having a stiffening system area that occupies significant portions of the backing area of the backing layer (for example, 50% or more, 60% or more, 70% or more, 80% or more, 90% or more, 95% or more, or even all of the backing area) may assist in providing support to the backing layer during both delivery of a medical dressing to a surface and/or after placement of a medical dressing on a surface.

The stiffening system perimeter 46 may define a stiffening system area that occupies less than all of the backing area defined by the first major surface 22 and/or second major surface 24 of the backing layer 20. In one or more embodiments, the stiffening system may have a stiffening system perimeter that defines a stiffening system area that occupies 95% or less, 85% or less, 75% or less, or even 65% or less of the backing area of the backing layer.

The stiffening system area defined by a stiffening system perimeter may occupy significant portions of the backing area of the backing layer. The stiffening systems described herein may include an array of stiffening elements arranged to provide desired mechanical support to the backing layer. The stiffening elements of the stiffening systems do not, however, completely occupy significant portions of the backing layer as compared to conventional approaches to limiting stretching of elastic backing layers of medical dressings. In contrast, the stiffening elements of stiffening systems may, in one or more embodiments, be described as occupying, within the stiffening system area defined by a stiffening system perimeter (see, for example stiffening system perimeter 46 of medical dressing 10) 50% or less, 40% or less, 30% or less, 20% or less, 10% or less, or even 5% or less of the first and/or second major surface of the backing layer to which the stiffening system is fixedly attached. As a result, the remainder of the backing layer not occupied by a stiffening element of a stiffening system retains its moisture vapor permeability and other properties. In some embodiment, the stiffening system itself may include through-holes, cuts, slits, or perforations to further allow for moisture vapor permeability.

The stiffening systems of one or more embodiments of medical dressings described herein may also be described in terms of the minimum amount of the stiffening system area occupied by the stiffening elements of the stiffening system. The stiffening elements of stiffening systems may be described as occupying, within the stiffening system area defined by a stiffening system perimeter (see, for example stiffening system perimeter 46 of medical dressing 10) 2% or more, 4% or more, 6% or more, 8% or more, or even 10% or more of the first and/or second major surface of the backing layer to which the stiffening system is fixedly attached.

The stiffening system perimeter 46 may be located or spaced inwardly from backing layer perimeter 26 as seen in FIG. 1, for example. In such an embodiment, the stiffening system perimeter 46 and backing layer perimeter 26 may be described as defining a border extending around the perimeter of the backing layer 20. The border may be defined, with respect to the embodiment in FIG. 1 as the area of the backing layer 20 located outside of the stiffening system perimeter 46. The absence of the stiffening system within that border between the stiffening system perimeter 46 and backing layer perimeter 26 may facilitate attachment of the medical dressing 10 to a surface due to the increased flexibility of the backing layer 20 outside of the stiffening system perimeter 46.

The embodiment of medical dressing 10 includes a border defined by the stiffening system perimeter 46 and the backing layer perimeter 26 that extends continuously around the perimeters 46 and 26 and is substantially uniform in width (where, in this instance, width is measured radially from the geometric centers 21/41). In one or more embodiments, however, such a border may not extend continuously around the stiffening system perimeter 46 and/or may not have a uniform width.

Although the stiffening system/region perimeter 46 is depicted as being spaced inwardly from the backing layer perimeter 26 such that a border is formed between the stiffening system/region perimeter 46 and the backing layer perimeter 26, in one or more embodiments, at least a portion or all of the backing layer 20 may extend only to the stiffening system/region perimeter 46 such that the stiffening system/region perimeter 46 and the backing layer perimeter 26 are coincident or coextensive with each other around the perimeter of the medical dressing 10. This may be true with respect to any one or more of the embodiments of medical dressings.

In the embodiment of medical dressing 10, the stiffening elements 42 may be described as being positioned proximate the geometric center 21 of the backing layer 20. Each stiffening element 42 includes a first or innermost end 44 located proximate the geometric center 21 of the backing layer and a second or outermost end 49 located distal from the first end of the stiffening element 42. The second or outermost end 49 of the stiffening element 42 may also be described as being located closer to the perimeter 26 of the backing layer 20 than the first or innermost end of the stiffening element 42.

The stiffening elements 42 may be described as having first and second ends located distal from each other, with the first ends 44 of each stiffening element 42 being located closer to the geometric center of the backing layer than the second ends 49, such that the second end of each stiffening element 42 is located closer to the perimeter 26 of the backing layer 20 than the first end. Each stiffening element 42 also includes a length defining a stiffening axis extending from the first end 44 to the second end 49 of the stiffening element 42, wherein a width of the stiffening element 42 as measured transverse to the length that is less than the length. Further, the stiffening axis of each stiffening element 42 extends away from the first end and towards the perimeter 26 of the backing layer 20.

Another feature of one or more embodiments of medical dressings that is depicted in connection with medical dressing 10 is found in the connection of the first or innermost ends of the stiffening elements 42 to each other within the stiffening system. Connections between the first or innermost ends 44 of the stiffening elements 42 to each other within the stiffening system is, however, optional. In one or more embodiments, the first or innermost ends of the stiffening elements 42 may merely abut up to each other with no actual physical connection between the ends of the stiffening elements 42. In still other embodiments, the first or innermost ends of the stiffening elements 42 may be fixedly attached by a frangible connection to facilitate placement of the stiffening system on the backing layer, with those frangible connections being broken relatively easily in response to tensile forces exerted on the composite of the backing layer 20 and stiffening system formed by stiffening elements 42.

Also, in the embodiment of medical dressing 10, each stiffening element 42 may be described as having a length defining a stiffening axis (one example of which is depicted as axis 11 in FIGS. 1-2). The length of each of the stiffening elements 42 (and the associated stiffening axis) extends from the first end 44 to the second end 49 of each stiffening elements 42.

Each of the stiffening elements 42 may also be described as having a width measured transverse to the length of the stiffening element 42 (and/or the stiffening axis defined by that stiffening element 42). The width of each of the stiffening elements 42 is, in one or more embodiments, less than the length of that stiffening element 42. In one or more embodiments, two or more stiffening elements 42 of the stiffening system may be described as having a uniform width along the length of each stiffening element 42. Stiffening elements with uniform widths are not, however, required for stiffening systems as used in medical dressings described herein. Further, although all of the stiffening elements 42 have the same or uniform width, in one or more embodiments, the widths of two or more stiffening elements may be different (for example, one or more stiffening elements may have a width that is different than one or more other stiffening elements).

In the embodiment of medical dressing 10, the stiffening axis defined by each of the stiffening elements 42 may be described as extending away from the geometric center 21 of the backing layer 20 and towards the perimeter 26 of the backing layer 20. More specifically, the embodiment of medical dressing 10 includes stiffening elements 42 that extend radially away from the geometric center 21 of the backing layer 20. In the embodiment of FIG. 1, medical dressing 10 includes a circular backing layer yielding a radially symmetric medical dressing. Stiffening system 40 is radially symmetric and centered on backing layer 20. The radial symmetric stiffening system can reduce movement of an underlying medical device disposed between the medical dressing and the patient's skin.

Stiffening elements used in stiffening systems of medical dressings, may include stiffening elements arranged in radial patterns as depicted in, for example, FIG. 1.

The backing layers used in one or more embodiments of medical dressings may be both elastic and provide a sufficiently impermeable barrier to the passage of liquids and at least some gases to protect a covered site from external contaminants. Elasticity allows the backing layer to expand, contract, stretch and recover as an underlying substrate, such as, e.g., skin, moves, and/or to conform to the shape of an underlying surface or article (for example, tubing, a catheter hub, etc.).

The physical characteristics of the backing layers and stiffening systems may be described with respect to the physical characteristics of the materials used to form the backing layers and/or stiffening systems or may be described with respect to the physical characteristics of the backing layers and/or stiffening systems as formed into discrete objects. Regardless of the specific manner in which the physical characteristics of the backing layers, stiffening systems, and stiffening system/backing layer composites are described, the stiffening systems provide additional rigidity and resistance to deformation of the backing layers to which they are applied. The following discussions are provided, therefore, only to assist in an understanding of the relative properties of the backing layers and stiffening systems used in one or more embodiments of the medical dressings described herein.

Young's Modulus of Elasticity

In one or more embodiments of the medical dressings described herein, the materials used to form the backing layers and stiffening support systems may be described in terms of the Young's Modulus of Elasticity for the different materials relative to each other. For example, the materials used to form the backing layers have a relatively low modulus of elasticity (for example, such that the backing layer exhibits elasticity when subjected to tensile forces along in-plane directions aligned with one or both of the first and second major surfaces of the backing layer). The materials used to form the stiffening elements of stiffening systems may have a relatively high modulus of elasticity when subjected to tensile forces along in plane directions aligned with one or both of the first and second major surfaces of the backing layer and, in some instances, with the stiffening axes of the stiffening elements, such that the stiffening system elements exhibit less elasticity than the backing layer. As a result, where the stiffening system of a medical dressing is fixedly attached to the backing layer (forming a stiffening system/backing layer composite) the stiffening system restrains the backing layer such that the stiffening system/backing layer composite exhibits a modulus of elasticity that is greater than the modulus of elasticity of the backing layer alone when subjected to tensile forces along in plane directions aligned with one or both of the first and second major surfaces of the backing layer and the stiffening axes of the stiffening elements.

Flexural Rigidity

The backing layers and stiffening systems of one or more embodiments of medical dressings may be described in terms of Flexural Rigidity which combines the Young's modulus of elasticity of the materials used for the different components with their geometry or shape. Flexural Rigidity may be generally described as the product (for example, $E*I$) of Young's modulus of elasticity (E) with the moment of inertia (I). In general, flexural rigidity may be used to describe the relative resistance to bending the backing layers, stiffening systems, and/or backing layer/stiffening system composites of one or more embodiments of medical dressings.

In one or more embodiments, the flexural rigidity of a stiffening element of a stiffening system of a medical dressing is greater than the flexural rigidity of the portion of the backing layer directly adjacent to the stiffening element (where, by directly adjacent, we mean the portion of the backing layer surface occupied by the stiffening element). In one or more embodiments of medical dressings including a backing layer and stiffening system, the flexural rigidity of the stiffening elements of the stiffening system may be 5 or more, 10 or more, 20 or more, 50 or more, 100 or more times the flexural rigidity of the portion of the backing layer directly adjacent to the stiffening elements of the stiffening system.

Where used to describe stiffening systems having stiffening elements that are a composite of two or more different materials and/or discrete objects attached, bonded, coalesced, etc. together to form the stiffening elements, flexural rigidity of such stiffening elements may be described in aggregate based on the stiffening element as a whole rather than the different materials and/or discrete objects used to form the stiffening element.

Elongation at Break

Elongation at break may be used to describe physical properties of the backing layers, stiffening systems, and/or backing layer/stiffening system composites of medical dressings described herein in response to forces acting on the backing layer and attached stiffening elements of a stiffening system in directions aligned with the major surfaces of the backing layer (sometimes referred to as "in-plane" directions) and, in the case of stiffening elements, along the stiffening axis of the stiffening element. Although the medical dressings described herein are not intended to be deformed sufficiently to break during use, elongation at break provides a potentially useful manner in which the relative physical characteristics of the backing layers and stiffening systems used in medical dressings. The elongation at break of the portions of the backing layer directly adjacent an attached element of a stiffening system of a medical dressing is higher than the elongation at break of the attached element of the stiffening system (as measured in the same directions on any given medical dressing).

In one or more embodiments, the portion of the backing layer directly adjacent to a stiffening element of the stiffening system has an elongation to break of at least 200% (independent of the stiffening system element fixedly attached to that portion of the backing layer). In one or more embodiments, the portion of the backing layer directly adjacent to a stiffening element of the stiffening system has an elongation to break of 800% or less (independent of the stiffening system element fixedly attached to that portion of the backing layer).

While the portions of the backing layers directly adjacent one or more of the attached elements of the stiffening systems exhibit elongation to break as discussed above, in one or more embodiments, one or more elements of the stiffening systems (independently of the backing layer) have essentially no elasticity, such that the one or more elements do not stretch before breaking and/or do not recover after being stretched along their stiffening axes. In one or more embodiments, one or more elements of the stiffening systems (independent of the backing layer) have an elongation to break of at least 5%. In one or more embodiments, one or more elements of stiffening systems (independent of the backing layer) have an elongation to break of 10% or more. In one or more embodiments, one or more elements of the stiffening systems (independent of the backing layer) have an elongation to break less than 200%. In one or more embodiments, one or more elements of the stiffening systems (independent of the backing layer) have an elongation to break of 100% or less, 50% or less, 20% or less, or even 10% or less.

One or more stiffening elements of the stiffening systems described herein may, in one or more embodiments, be more elastic in one direction than another direction. For example, the elongation at break of a given stiffening element of a stiffening system along a length of the stiffening element may be greater than the elongation at break of that same element along the width of the stiffening element (where the width is less than the length). In one or more embodiments, the elongation at break in an in-plane direction of such stiffening elements of a stiffening system may still be less than the elongation at break of the fixedly attached portions of the backing layer in the same direction.

Symmetry

Controlling undesirable stresses on around invasive medical devices can improve patient comfort and ultimately benefit patient outcomes. The undesirable stresses or forces can be caused by movement of the patient or by routine care and maintenance by a clinician. It would be desirable to secure a medical device so that it does not move in a way that would cause the patient discomfort.

In some embodiments, the stiffening systems and/or the medical dressing can have a degree of symmetry. The stiffening systems can be radially symmetric, bilaterally symmetric, uniaxially symmetric or nonsymmetric while the medical dressings are typically radially symmetric, bilaterally symmetric. Radially symmetric stiffening systems can help mitigate stresses on the backing layer around a substantial portion of a medical device's circumference or a wound which can reduce undesirable elongation or flexing in the backing that in some embodiments provide a means of holding a medical device in a desired location without needing to adhesively attach the device directly to a patient's skin. Bilaterally symmetric or nonsymmetric stiffening systems help manage stresses in a predefined way. For example, it is possible to have a stiffening system that limits elongation of the backing in one direction while allowing elongation or flexing of the backing in a second direction (See for example FIGS. 18 and 19. In some embodiments, this type of control can be useful when a medical dressing is placed over a device or a wound near a joint or other location where it is more important to preferentially mitigate stresses in a particular direction or location.

The symmetry of the stiffening system and the medical dressing can be the same (i.e. both can be radially symmetric, for example, see FIG. 1, or bilaterally symmetric) or the symmetries can be different such as by having a radially symmetric stiffening element disposed on a bilaterally symmetric medical dressing, see for example FIG. 24, 26A or 31A-31D.

Some potential variations of those features and/or characteristics will now be described to provide a more complete understanding of the medical dressings described herein. FIGS. 4-11 depict various embodiments of radially symmetric stiffening systems that may be used in connection with one or more embodiments of medical dressings. When used, these stiffening systems will reduce movement of a medical device disposed under the stiffening system of an exemplary medical dressing having one of said stiffening systems. Varying the graphical pattern of the stiffening system can improve spatial positioning of the medical device beneath the medical dressing.

Figure 4:
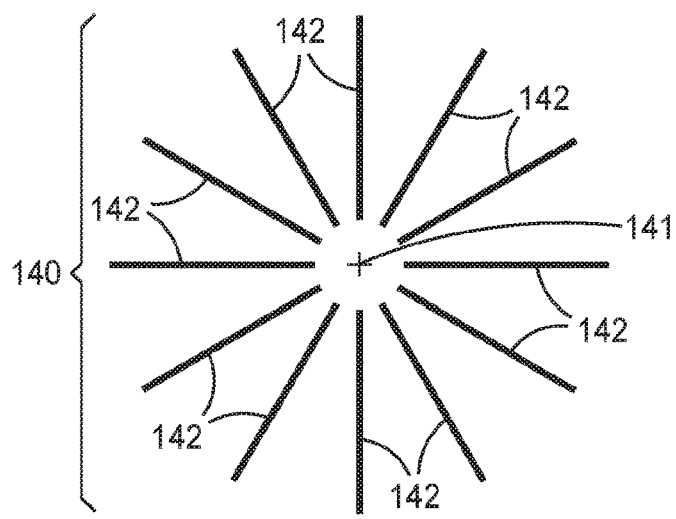
FIGS. 4-11 depict embodiments of stiffening systems that may be used with one or more embodiments of medical dressings.

FIG. 4 depicts a stiffening system 140 that includes stiffening elements 142 extending outward from a geometric center 141 of the stiffening system 140. Stiffening elements 142 are arranged to extend radially outward from the geometric center 141 of stiffening system 140. Although not depicted, each of the stiffening elements 142 would define a stiffening axis that extends radially outward from the geometric center 141 of the stiffening system 140.

One difference between stiffening system 140 including stiffening elements 142 and the stiffening system described above in connection with the embodiment of the stiffening system used with medical dressing 10 is that the first or innermost ends of the stiffening elements 142 (the ends of stiffening elements 142 located closest to the geometric center 141) are spaced apart from each other. Such an arrangement may, for example, provide a stiffening system that allows for more elasticity of the attached backing layer proximate the geometric center 141 of the stiffening system than the arrangement of stiffening elements 42 with respect to the stiffening system of medical dressing 10.

Figure 5:
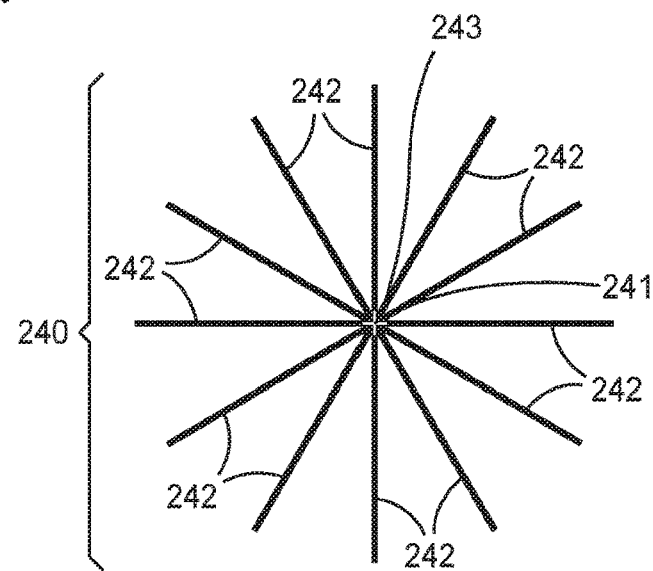

FIG. 5 depicts a stiffening system 240 that includes stiffening elements 242 also extending outward from a geometric center 241 of the stiffening system 240. Stiffening elements 242 are arranged to extend radially outward from the geometric center 241 of the stiffening system 240. Although not depicted, each of the stiffening elements 242 defines a stiffening axis that extends along a length of each of the stiffening elements 242.

One difference between stiffening system 240 including stiffening elements 242 and the stiffening system described above in connection with the embodiment of the stiffening system used with medical dressing 10 is that the first or innermost ends of the stiffening elements 242 (the ends of stiffening elements 242 located closest to the geometric center 241) are attached to a central support 243 proximate the geometric center 241 of the stiffening system 240. Although all of the first or innermost ends of the stiffening elements 242 are depicted as being attached to the central support 243, in one or more embodiments one or more of the stiffening elements 242 may be detached from the central support 243. Further, although the geometric center 241 of the stiffening system 240 is depicted as being located at a center of the central support 243, such an arrangement is not required. For example, the geometric center 241 may be located outside of the central support 243. In another example, the central support 243 may define its own geometric center and that geometric center may be at a different location than the geometric center 241 of the stiffening system 240 as a whole.

One potential advantage of a stiffening system including a central support 243 is that the central support 243 may improve the structural integrity of the stiffening system 240 as a whole due to connections made between the set of stiffening elements 242 connected to the central support 243. Another potential advantage of stiffening systems such as stiffening system 240 is that the connections between the stiffening elements 242 and the central support 243 may assist in placement of the stiffening system 240 relative to a backing layer. Another potential advantage of stiffening systems such as stiffening system 240 is that the central support 243 may provide a visual indicator of a center of the stiffening system 240, which may assist a user in placing a medical dressing carrying the stiffening system 240 at a selected location.

Figure 6:
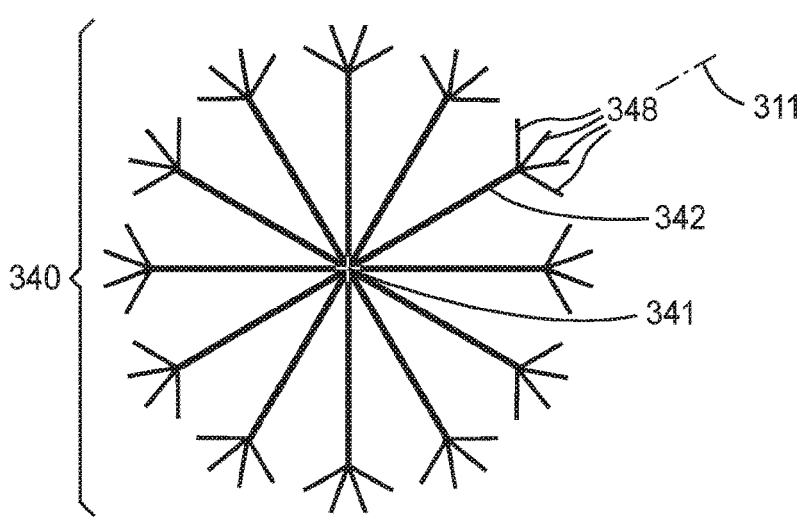

FIG. 6 depicts a stiffening system 340 including stiffening elements 342 also extending outwardly from a geometric center 341 of the stiffening system 340. Stiffening elements 242 are arranged to extend radially outward from the geometric center 341 of the stiffening system 340. Although not depicted, each of the stiffening elements 342 also defines a stiffening axis that extends along a length of each of the stiffening elements 342 (see, for example, stiffening axis 311).

One difference between the stiffening system 340 including stiffening elements 242 and the stiffening systems described above is that the stiffening elements 342 include branches 348 extending outwardly away from the stiffening axes (for example, stiffening axis 311) proximate the second ends of the stiffening elements 342. In the embodiment, the branches 348 may also be described as extending from the stiffening element 342 and towards a perimeter of a backing layer (not shown) on which the stiffening system 340 is fixedly attached.

One or more embodiments of stiffening systems may or may not include branches extending from one or more stiffening elements of the stiffening system. One or more embodiments of stiffening systems may include different sets of branches extending from the stiffening elements.

One potential advantage of providing branches 348 extending from the stiffening elements of stiffening systems may be to provide additional support to a backing layer at the perimeter of the stiffening system 340. Another potential advantage of providing branches 348 extending from the stiffening elements of stiffening systems may be to disperse forces that may otherwise be concentrated at the second or outermost ends of the stiffening elements 342.

Figure 7:
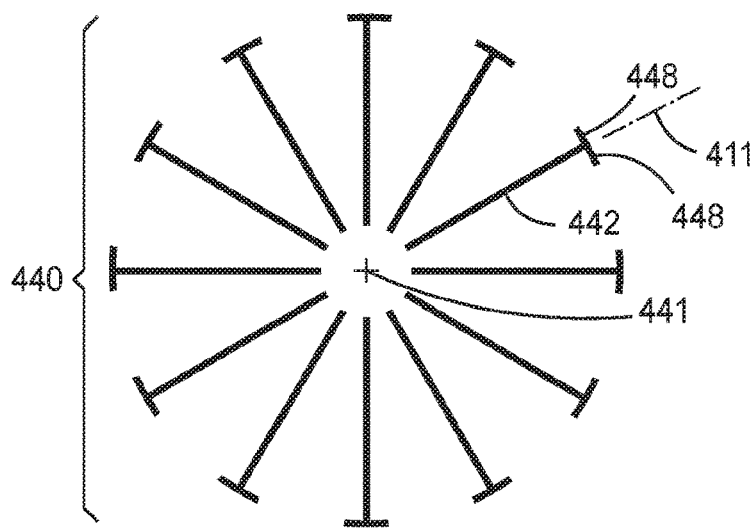

FIG. 7 depicts another stiffening system 440 that includes stiffening elements 442 also extending outwardly from a geometric center 441 of the stiffening system 440. Stiffening elements 442 are arranged to extend radially outward from the geometric center 441 of the stiffening system 440. Although not depicted, each of the stiffening elements 442 defines a stiffening axis that extends along a length of each of the stiffening elements 442 (see, for example, stiffening axis 411).

One difference between stiffening system 440 including stiffening elements 442 and the stiffening systems described above is that the stiffening elements 442 include branches 448 extending away from the stiffening axes (for example, stiffening axis 411) proximate the second ends of the stiffening elements 442.

Although each of the stiffening elements 442 includes branches 448 extending therefrom, one or more embodiments of stiffening systems may or may not include branches extending from one or more stiffening elements of the stiffening system. Further, although the sets of branches extending from the stiffening elements 442 are depicted as being uniform over the entire set of stiffening elements, one or more embodiments of stiffening systems may include different sets of branches extending from the stiffening elements.

One potential advantage of providing branches 448 extending from the stiffening elements 442 may be to provide additional support to a backing layer at the perimeter of the stiffening system 440. Another potential advantage of providing branches 448 extending from the stiffening elements 442 may be to disperse forces that may otherwise be concentrated at the second or outermost ends of the stiffening elements 442.

Figure 8:
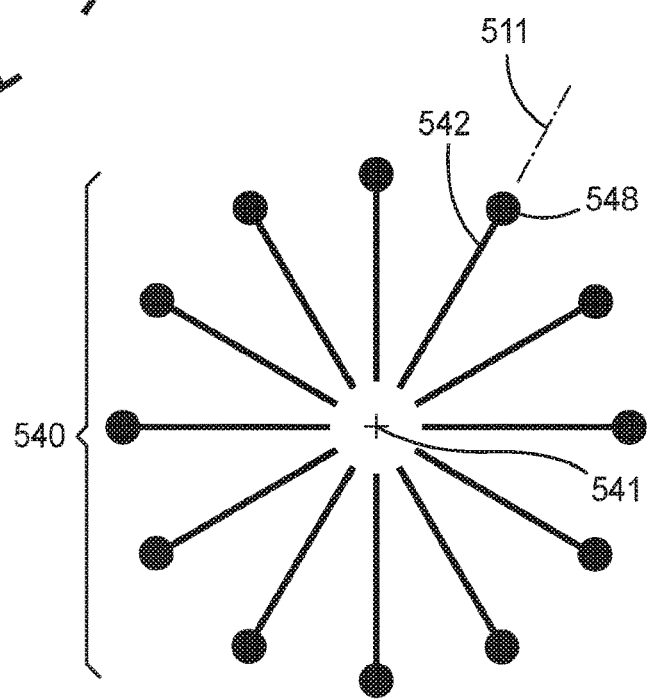

FIG. 8 depicts another stiffening system 540 that includes stiffening elements 542 also extending generally outward from a geometric center 541 of the stiffening system 540. Stiffening elements 542 are arranged to extend radially outward from the geometric center 541 of the stiffening system 540. Although not depicted, each of the stiffening elements 542 again defines a stiffening axis that extends along a length of each of the stiffening elements 542 (see, for example, stiffening axis 511).

One difference between stiffening system 540 including stiffening elements 542 and the stiffening systems described above is that stiffening elements 542 include pads 548 located at the second or outermost ends of the stiffening elements 542 that provide support for a backing layer fixedly attached thereto in directions that extend away from the stiffening axes (for example, stiffening axis 511) at the second ends of the stiffening elements 542.

One or more embodiments of stiffening systems may or may not include pads at the second or outermost ends of one or more of the stiffening elements of the stiffening system. Further, one or more embodiments of stiffening systems may include different pads at the second or outermost ends of one or more of the stiffening elements 542.

One potential advantage of providing pads 548 at the second or outermost ends of the stiffening elements 542 may be to provide additional support to a backing layer at the perimeter of the stiffening system 540. Another potential advantage of providing pads 548 at the second or outermost ends of the stiffening elements 542 may be to disperse forces that may otherwise be concentrated at the second or outermost ends of the stiffening elements 542.

Figure 9:
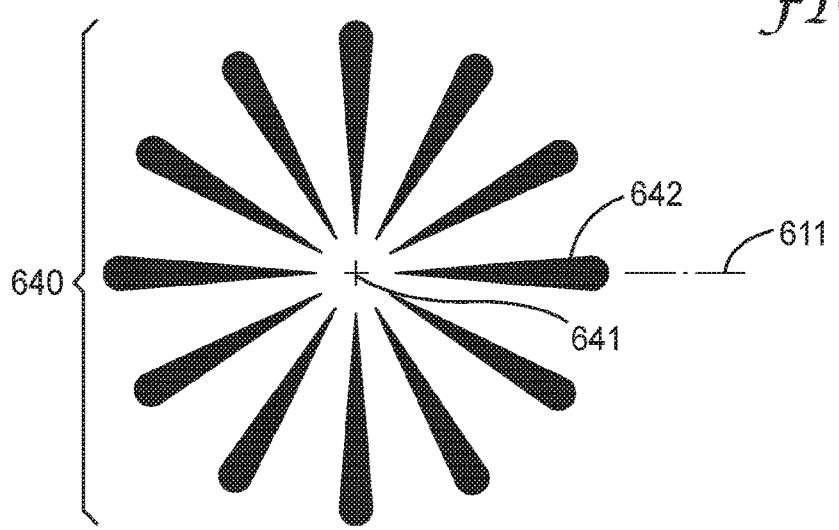

FIG. 9 depicts another stiffening system 640 that includes stiffening elements 642 also extending generally outward from a geometric center 641 of the stiffening system 640. Stiffening elements 642 are arranged to extend radially outward from the geometric center 641 of the stiffening system 640. Although not depicted, each of the stiffening elements 642 again defines a stiffening axis that extends along a length of each of the stiffening elements 642 (see, for example, stiffening axis 611).

One difference between stiffening system 640 including stiffening elements 642 and the stiffening systems described above is that stiffening elements 642 do not have a uniform width along their length. In the embodiment, each of the stiffening elements 642 gets wider when moving along the stiffening axis from the first or innermost end (proximate the geometric center 641 of the stiffening system 640) towards the second or outermost end of the stiffening element 642. As the width of each of the stiffening elements 642 changes, so does the flexural rigidity of each of the stiffening elements 642. When the width of the stiffening element 642 reduces smoothly to zero, for example, the flexural rigidity of the stiffening element 642 may also be uniformly reduced to match the flexural rigidity of the backing layer 620 at that location. Further, although all of the stiffening elements 642 have the same or uniform shape, in one or more embodiments, the shapes of two or more stiffening elements may be different (for example, one or more stiffening elements may have a shape that is different than one or more other stiffening elements).

One or more embodiments of stiffening systems may include one or more stiffening elements that do not get wider when moving outward from the center of the stiffening system 640. One or more embodiments of stiffening systems may include stiffening elements that are different from one or more other stiffening elements of a stiffening system.

One potential advantage of providing stiffening elements that widen when moving outward from a center of the stiffening system is that additional support may be provided to a backing layer proximate the perimeter of the stiffening system 640. Another potential advantage of providing stiffening elements that widen when moving outward from a center of the stiffening system is that forces along a length of the stiffening elements may be dispersed at the second or outermost ends of the stiffening elements 642.

Figure 10:
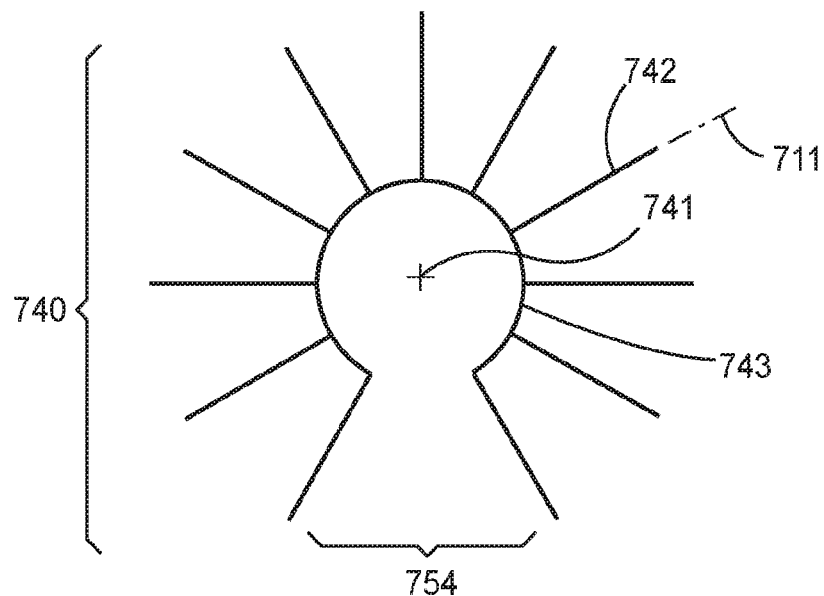
Figure 11:
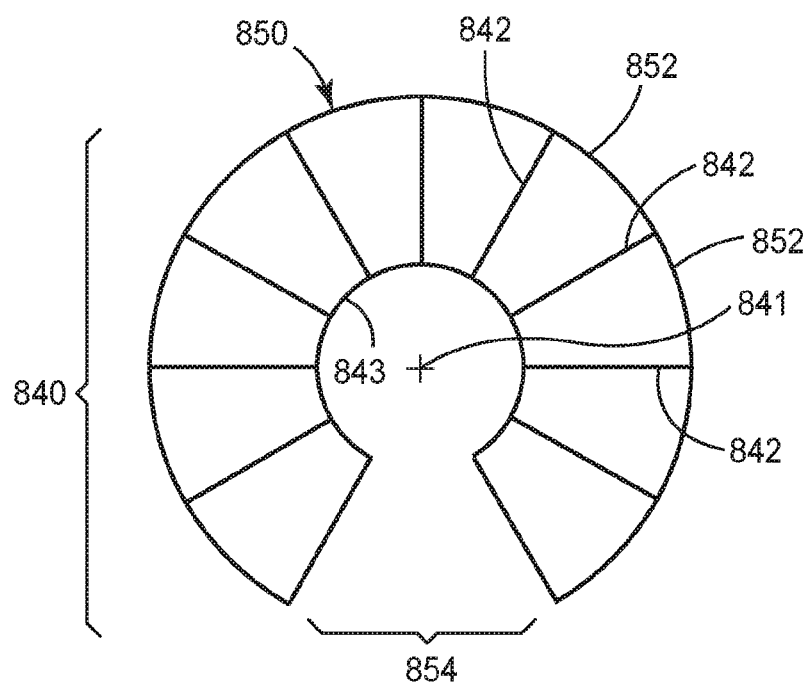

FIGS. 10 and 11 illustrate stiffening systems 740, 840 which are substantially radially symmetric. However, each of these stiffening systems 740, 840 has a stiffening system gap 754, 854 occupying an arc about the center of the stiffening system. The stiffening system gap can provide a region of greater elasticity in an otherwise radially symmetric stiffening member.

FIG. 10 depicts a stiffening system 740 including stiffening elements 742 also extending outward from a center 741 of the stiffening system 740. Stiffening elements 742 are arranged to extend radially outward from the center 741 of the stiffening system 740. Although not depicted, each of the stiffening elements 742 also defines a stiffening axis that extends along a length of each of the stiffening elements 742 (see, for example, stiffening axis 711).

Stiffening system 740 includes a central support 743, with the first or innermost ends of the stiffening elements 742 (the ends of the stiffening elements 742 located closest to the center 741) are attached to the central support 743. One or more embodiments, one or more of the stiffening elements 742 may be detached from the central support 743.

One difference between the stiffening system 740 and stiffening systems described above is that the stiffening system does not extend completely around the center 741. Rather, the stiffening system 740 includes a stiffening system gap 754 occupying an arc about the center 741 that is free of stiffening elements. Such an arrangement may, for example, be useful where the stiffening system 740 is to be used to secure a catheter or other article having any component extending outwardly away from the center 741 of the stiffening system 740. In particular, stiffening system gap 754 may accommodate tubing connected to a catheter hub located beneath the stiffening system 740.

The stiffening system gap 754 may occupy any selected arc relative to a center 741 of the stiffening system 740. In one or more embodiments, the stiffening system gap 754 may occupy an arc of, for example, 10° or more, 15° or more, 20° or more, 25° or more, 30° or more, 40° or more, 50° or more, or even 60° or more. In one or more embodiments the stiffening system gap 754 may occupy an arc having an upper limit of, for example, 180° or less, 150° or less, 120° or less, 90° or less, 80° or less, 70° or less, 60° or less, 50° or less, 40° or less, or even 30° or less.

The gaps provided in stiffening systems of medical dressings may be described in terms of the actual size of the gap. The actual size of the gap may be selected based on the intended use of the medical dressing, for example, on the relative size of any tubing expected to pass through the gap, etc. With respect to the embodiment of stiffening system 740 including stiffening system gap 754, the minimum distance between the stiffening elements defining the boundaries of the stiffening system gap 754 may, in one or more embodiments, be 5 mm or less, 10 mm or less, 15 mm or less, 20 mm or less, 30 mm or less, 40 mm or less, or 50 mm or less. The maximum distance between the stiffening elements defining the boundaries of the stiffening system gap may, in one or more embodiments, the 100 mm or less, 90 mm or less, 80 mm or less, 70 mm or less, 60 mm or less, 50 mm or less, 40 mm or less, 30 mm or less, 20 mm or less, or 10 mm or less.

FIG. 11 depicts a stiffening system 840 including stiffening elements 842 also extending outward from a center 841 of the stiffening system 840. Stiffening elements 842 are arranged to extend radially outward from the center 841 of the stiffening system 840. Although not depicted, each of the stiffening elements 842 also defines a stiffening axis that extends along a length of each of the stiffening elements 842.

Stiffening system 840 also includes a central support 843 which is offset from the center 841 of stiffening system 840, with the first or innermost ends of the stiffening elements 842 (the ends of the stiffening elements 842 located closest to the center 841) attached to the central support 843. One or more of the stiffening elements 842 may be detached from the central support 843 via a frangible section (not shown).

One difference between the stiffening system 840 and stiffening system 740 depicted in FIG. 10 is that stiffening system 840 includes a perimeter support 850 formed by perimeter support elements 852 that, in the embodiment, extend between the second or outermost ends of adjacent pairs of stiffening elements 842. The perimeter support 850 may improve structural integrity of the stiffening system 840 and, in one or more embodiments, may provide additional support to a portion of a backing layer located outside of the stiffening system perimeter.

As in stiffening system 740, stiffening system 840 also includes a stiffening system gap 854, with the stiffening system gap being formed in both the central support 843 as well as the perimeter support 850.

Figure 12:
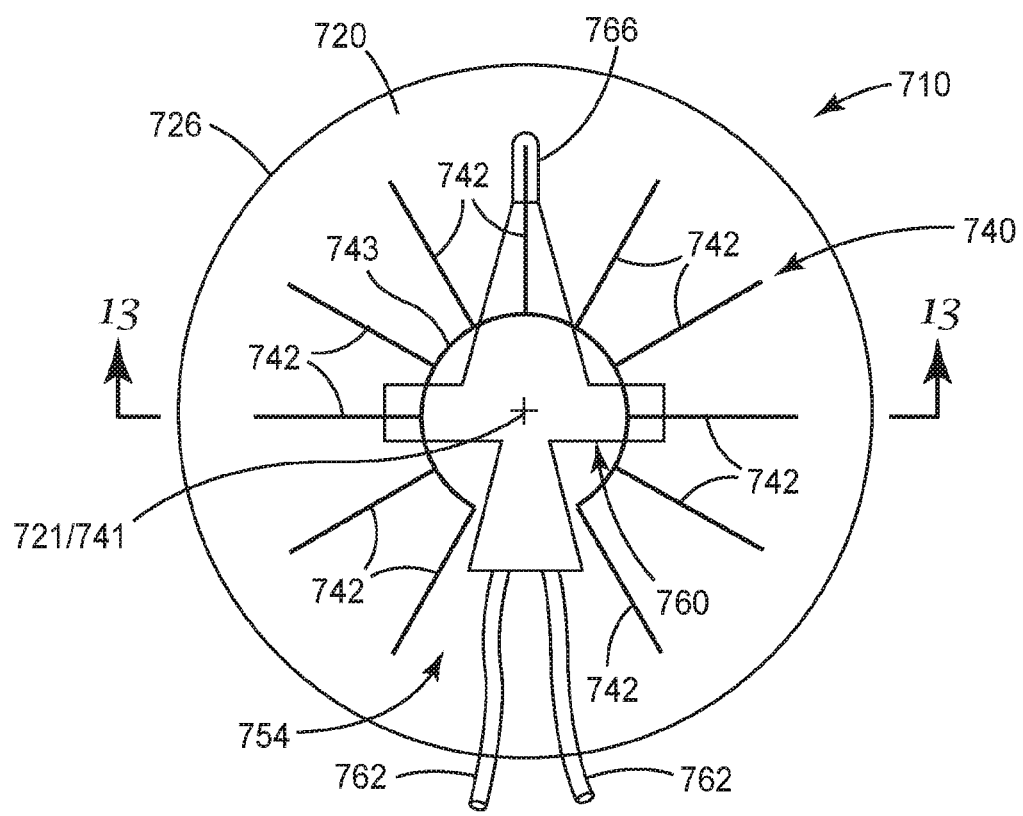
FIG. 12 is a top view of another embodiment of a medical dressing including a stiffening system as in FIG. 10 on a backing layer, with the medical dressing being placed over a medical device.

FIG. 12 is a top view of the partially radially symmetric stiffening system 740 of FIG. 10 fixedly attached to a radially symmetric backing layer 720 of another embodiment of a medical dressing 710. The medical dressing 710 is positioned over a medical device, for example, a catheter hub 760. Catheter hub 760 supports a catheter 766 and includes tubing 762 attached thereto for delivering and/or removing fluids through the catheter 766.

The backing layer 720 of medical dressing 710 includes a backing layer perimeter 726, with the stiffening system 740 centrally located on the backing layer 720 such that the center 741 of the stiffening system 740 is coincident with the center 721 of the backing layer 720 (although as discussed herein, those centers 721 and 741 need not necessarily be coincident in all medical dressings).

Stiffening elements 742 of stiffening system 740 extend outwardly from the central support 743 to provide support for the backing layer 720. A portion of the catheter hub 760 from which tubing 762 extends is located within the stiffening system gap 754 and, further, extends out from beneath the backing layer 720 to any suitable fluid delivery or management system via tubing 762.

Figure 13:
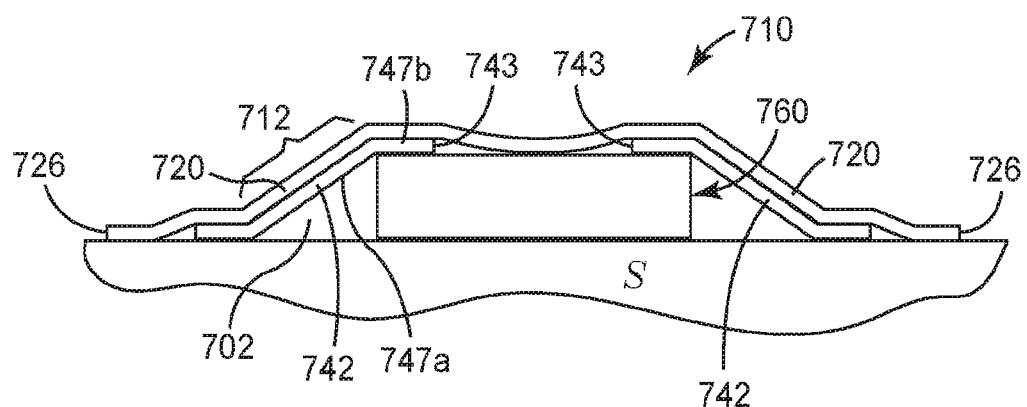
FIG. 13 is a cross-sectional view of the medical dressing of FIG. 12 taken along line 13-13 in FIG. 12.

FIG. 13 is a cross-sectional view of FIG. 12 taken along line 13-13 in FIG. 12 (with the interior details of the medical device or catheter hub 760 not provided because those details are not important with respect to the current invention). In some applications, the medical dressing 710 may be tented over medical device 760 such that portions of the medical dressing are unsupported (see unsupported portion 712 in FIG. 13) over free space 702 between where the medical dressing contacts the skin, S, of the patient and the medical device. In some conventional medical dressings, stress can be applied to the backing when the patient moves or when the clinician is checking the status of the medical devise. This stress can cause the backing to stretch and/or sag which can result in undesirable movement of the medical device.

It may, in one or more embodiments, be that the stiffening system extend from the skin, S, of the patient onto the catheter body 760 as seen in FIG. 13 to provide additional structural support to the otherwise elastically extensible backing layer 720 in the unsupported portion 712 of medical dressing 710. The additional structural support may provide the medical dressing 710 with improved retention of the catheter hub 760 at a selected location on thee skin, S, of a patient.

In some embodiments, surface 747 of the stiffening elements 742 may be coated with an adhesive layer, such as adhesive layer 35 shown on surface 47a of stiffening element 42a in FIG. 2B or adhesive 30" disposed on surface 47" of stiffening element 42" in FIG. 3B allowing for stiffening elements 742 to be attached to both the patient's skin and the medical device such that the portion of the stiffening element(s) between these attachment points act as reinforcing beam to secure the medical device in a fixed location relative to the patient's skin and preventing stretching or sagging of the unsupported portions 712 of the elastic backing in the vicinity of the stiffening element(s).

Figure 14:
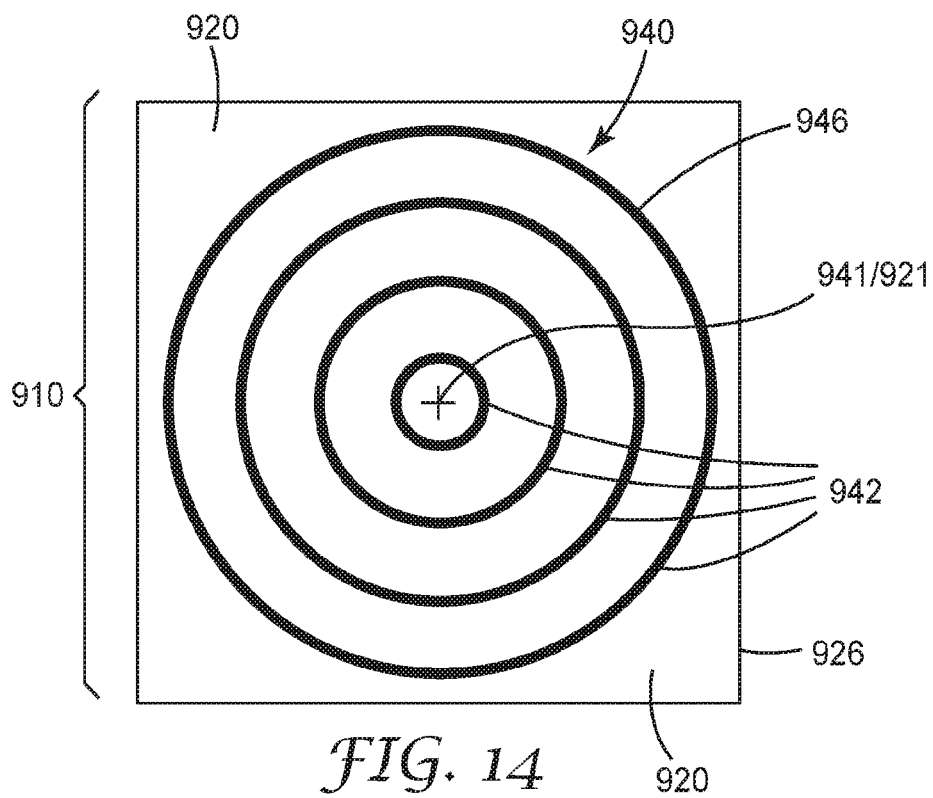
FIGS. 14-15 are top views of a embodiments of medical dressings including stiffening systems on a backing layer.
Figure 15:
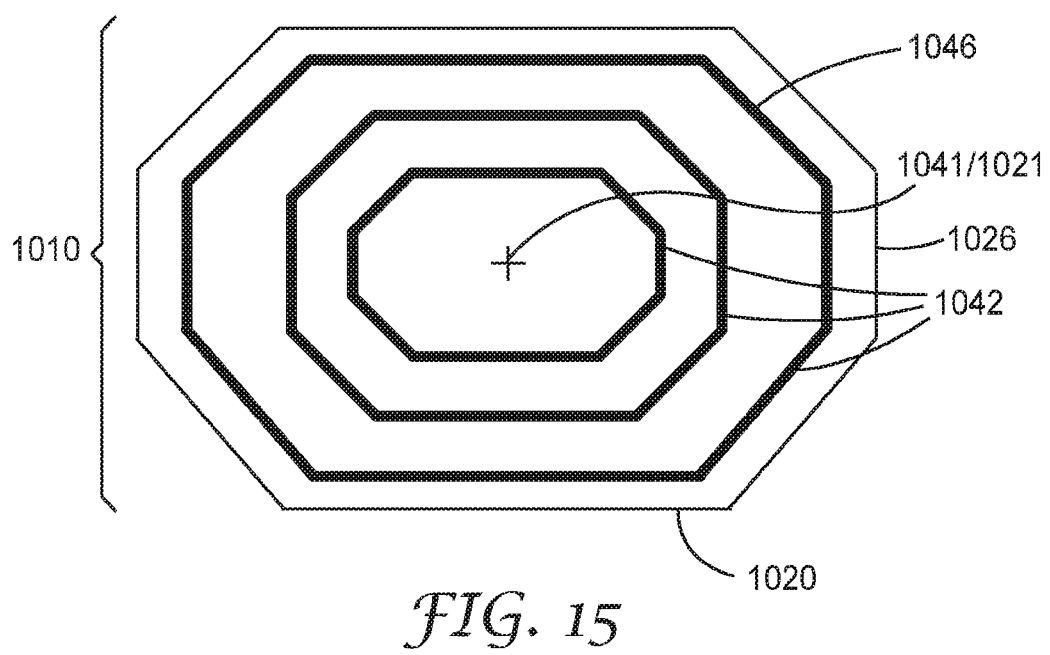

FIGS. 14-15 are top views of embodiments of medical dressings including stiffening systems on backing layers. The stiffening systems are generally in the form of concentric stiffening elements on the backing layers.

FIG. 14 depicts a medical dressing 910 including a backing layer 920. The backing layer 920 includes a backing layer perimeter 926 and also defines a geometric center 921. The stiffening system on medical dressing 910 includes radially symmetric stiffening elements 942 arranged concentrically on the backing layer 920. Backing layer 920 is generally rectangular yielding a medical dressing 910 that is bilaterally symmetric. The stiffening system including stiffening elements 942 defines a stiffening system center 941 that is coincident with the geometric center 921 of the backing layer 920, although coincidence between these center points is not required in medical dressings.

In the embodiment of medical dressing 910, the stiffening elements 942 each define a ring having a radial width less than a ring length. The radial width is defined along a radial axis extending outwardly from the center 941 of the stiffening system, while the ring length is defined along a line following a center of the radial width of each of the stiffening elements 942 when moving around the center 941.

One or more embodiments of stiffening systems used in medical dressings may include stiffening elements that have a nonuniform radial width over their ring length. Further, in one or more embodiments, the radial width of different stiffening elements within a stiffening system may be different for two or more of the stiffening elements (for example, the radial width of the outermost stiffening element may be greater than or less than the radial width of one or more other stiffening elements located within the outermost stiffening element).

In one or more embodiments of medical dressings including a set of concentric stiffening elements such as the stiffening elements 942, radial spacing between adjacent pairs of stiffening elements 942 within the stiffening system may be uniform as in FIG. 14 (where radial spacing between adjacent pairs of stiffening elements is measured along a radial axis extending outwardly from the center of the stiffening system). In one or more embodiments, radial spacing between different adjacent pairs of stiffening elements may be different within a stiffening system. In one or more embodiments, radial spacing between a single adjacent pair of stiffening elements may also vary where, for example, the stiffening elements themselves have shapes that are not circular.

The symmetric geometry of stiffening system 940 provides equal support to medical dressing 910 at all angles around the center 941 of the support system.

Another embodiment of a medical dressing 1010 is in FIG. 15. The medical dressing 1010 includes a backing layer 1020 having a backing layer perimeter 1026 that is bilaterally symmetric and defines a geometric center 1021 for the backing layer 1020. The medical dressing 1010 includes elongated octagonal stiffening elements 1042 arranged concentrically on the backing layer 1020 resulting in a bilaterally symmetric stiffening system. The bilateral support of stiffening system 1040 provides medical dressing with more support (i.e. the medical dressing is stiffer and subject to less elongation) in the vertical direction in FIG. 15 where the stiffening elements are disposed closer together than depicted in the horizontal direction. In the embodiment, the stiffening system elements 1042 define a stiffening system center 1041 that is coincident with the geometric center 1021 of the backing layer 1020.

One difference between the stiffening system in connection with medical dressing 1010 as compared to medical dressing 910 is that the stiffening elements 1042 of medical dressing 1010 are not circles. In the embodiment of medical dressing 1010, the stiffening elements 1042 are in the form of octagons, but any suitable shape may be used for stiffening elements arranged concentrically on medical dressings. Examples of potential shapes may include, for example, polygons (for example, triangles, squares, rectangles, etc.), ovals, ellipses, hexagons, etc. Virtually any regular or irregular shape could be used to provide concentrically arranged rings about a center of a stiffening system used to support a backing layer of a medical dressing.

Another feature in connection with medical dressing 1010 is that the stiffening system perimeter 1046 defined by the outermost stiffening element 1042 may match the shape of the backing layer perimeter 1026 of backing layer 1020. Doing so may provide support for the backing layer 1020 about its perimeter 1026 and that support may be beneficial during, for example, delivery of the medical dressing 1010 to the patient.

Further, all of the variations described herein with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.), may be provided in connection with stiffening systems having stiffening elements in the form of concentric rings as described in connection with FIGS. 14-15.

Figure 16:
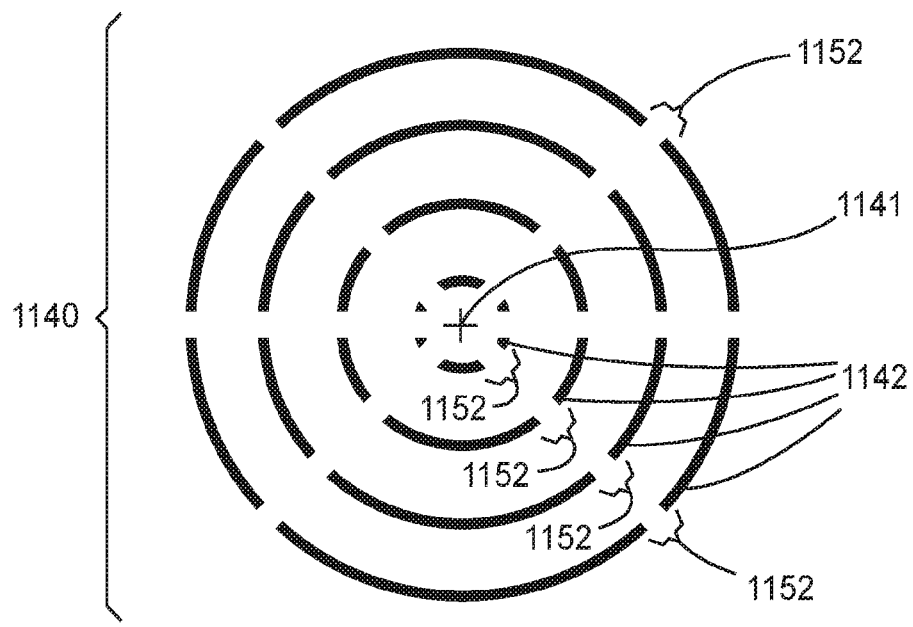
FIG. 16-17 depict embodiments of stiffening systems that may be used with one or more embodiments of medical dressings.
Figure 17:
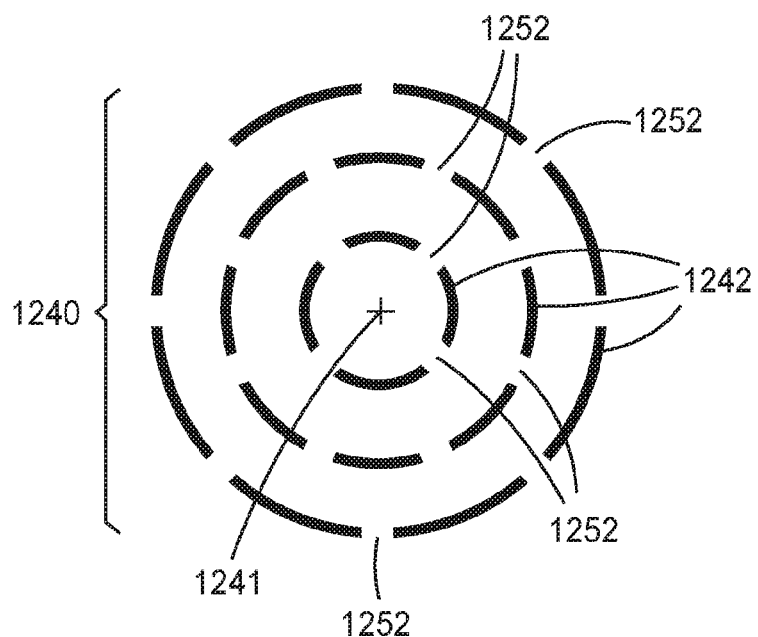

FIGS. 16-17 depict embodiments of stiffening systems that may be used in one or more embodiments of medical dressings. In addition to the variations described with respect to concentric ring stiffening systems provided on medical dressings 910 and 1010, the concentric ring stiffening systems in FIGS. 16-17 illustrate other potential variations in stiffening systems that may be provided on medical dressings.

The embodiment of stiffening system 1140 in FIG. 16 includes stiffening elements 1142 arranged concentrically around a center 1141 of the stiffening system 1140. While stiffening elements 942 and 1042 in, respectively, FIGS. 14-15 are in the form of continuous rings, stiffening system 1140 includes stiffening elements 1142 that are in the form of discontinuous rings, each of which includes discrete segments separated by gaps 1152. As a result, adjacent segments of each of the stiffening elements 1142 are separated by gaps 1152 when moving around the ring defined by each stiffening element 1142.

One feature in connection with the discontinuous rings formed by stiffening elements 1142 of stiffening system 1140 is that the gaps 1152 for at least one radially adjacent pair of stiffening elements 1142 are aligned along a radius extending outward from the center 1141 of the stiffening system 1140. Providing discontinuous rings that include, for example, gaps 1152 of stiffening system 1140, may allow the backing layer to which the stiffening system 1140 is fixedly attached to expand along in plane directions because the backing layer in the gaps 1152 is allowed to stretch. In one or more embodiments, radial alignment of the gaps in stiffening systems may make a medical dressing using such a stiffening system more conformable along, for example, any axis that is orthogonal to a radius of the stiffening system. Radial alignment of the gaps 1152 in the stiffening system 1140 may also possibly improve flexibility of an underlying backing layer about the radii along which the gaps 1152 are aligned.

The embodiment of stiffening system 1240 in FIG. 17 includes stiffening elements 1242 arranged concentrically around a center 1241 of the stiffening system 1240. As with stiffening elements 1142 of stiffening system 1140 in FIG. 16, stiffening system 1240 includes stiffening elements 1242 that are in the form of discontinuous rings, each of which includes discrete segments separated by gaps 1252. As a result, adjacent segments of each of the stiffening elements 1242 are separated by gaps 1252 when moving around the ring defined by each stiffening element 1242.

The stiffening elements 1242 of stiffening system 1240 differ from stiffening elements 1142 of stiffening system 1140 in that the gaps 1252 of at least one pair of radially adjacent stiffening elements 1242 of stiffening system 1240 are not aligned along a radius extending radially outward from the center 1241 of the stiffening system 1240. In other words, the gaps 1252 of at least one pair of radially adjacent stiffening elements 1242 do not lie along a single radius extending radially outward from the center 1241 of the stiffening system 1240. The arrangement of the gaps 1252 of at least one pair of radially adjacent stiffening elements 1242 may be described as being circumferentially offset with respect to each other. Radially misaligned (or circumferentially offset) gaps 1252 in the stiffening system 1240 may possibly improve support for an underlying backing layer to which the stiffening system 1240 is fixedly attached.

One or more embodiments of stiffening systems used in medical dressings may include combinations of both radially aligned and radially misaligned gaps to provide selected physical characteristics to an attached backing layer.

Further, all of the variations with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.), as well as stiffening elements in the form of concentric rings as described in connection with FIGS. 14-15 (for example, radial spacing between adjacent rings, variations in ring width, etc.) may be provided in connection with stiffening systems having discontinuous rings as in, for example, FIGS. 16-17.

FIGS. 18-21 are top views of embodiments of medical dressings including stiffening systems that define a stiffening axis using a plurality of stiffening elements in which each of the stiffening elements defines a longitudinal axis aligned with the stiffening axis of the stiffening system. Thus, these stiffening systems can be categorized as being uniaxially symmetric. One example of such a stiffening system is on a backing layer in FIGS. 18-19 or alone in FIGS. 20-21.

Figure 18:
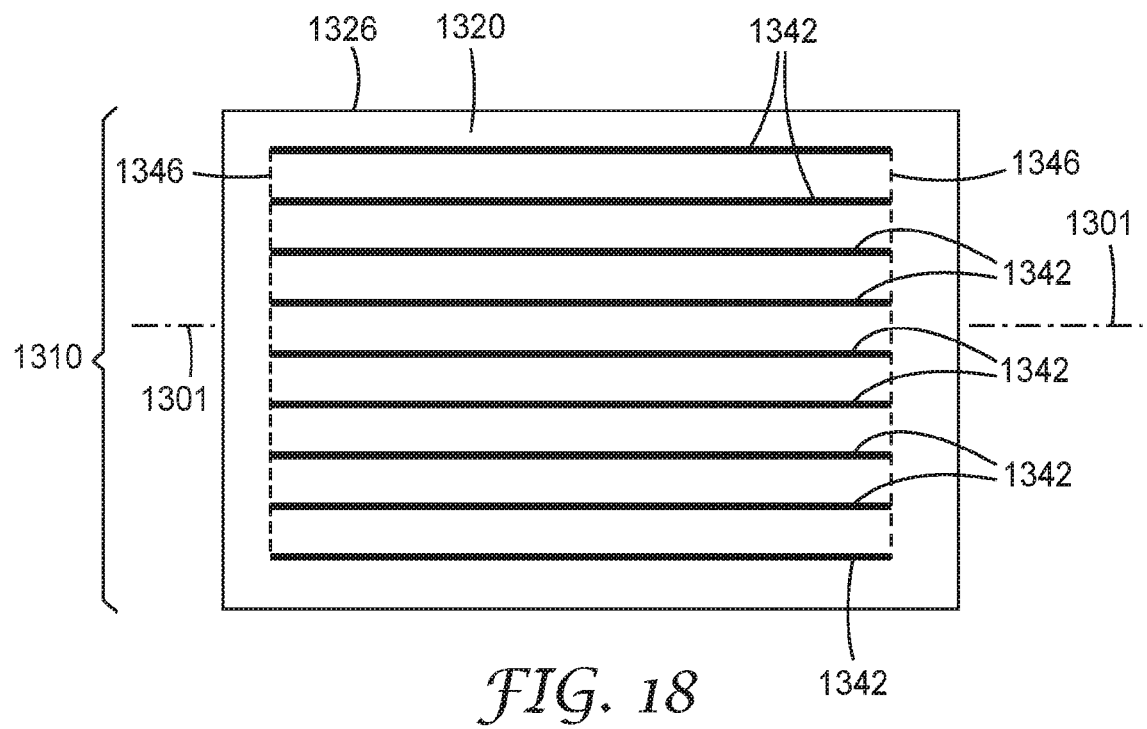
FIG. 18 is a top view of an embodiment of a medical dressing including a stiffening system.

FIG. 18 depicts a medical dressing 1310 including a backing layer 1320 having a backing layer perimeter 1326. The medical dressing 1310 includes a stiffening system including multiple stiffening elements 1342. Each of the stiffening elements 1342 extends between first and second ends such that the stiffening element 1342 defines a longitudinal axis extending through those first and second ends and a width measured transverse to the longitudinal axis.

Figure 19:
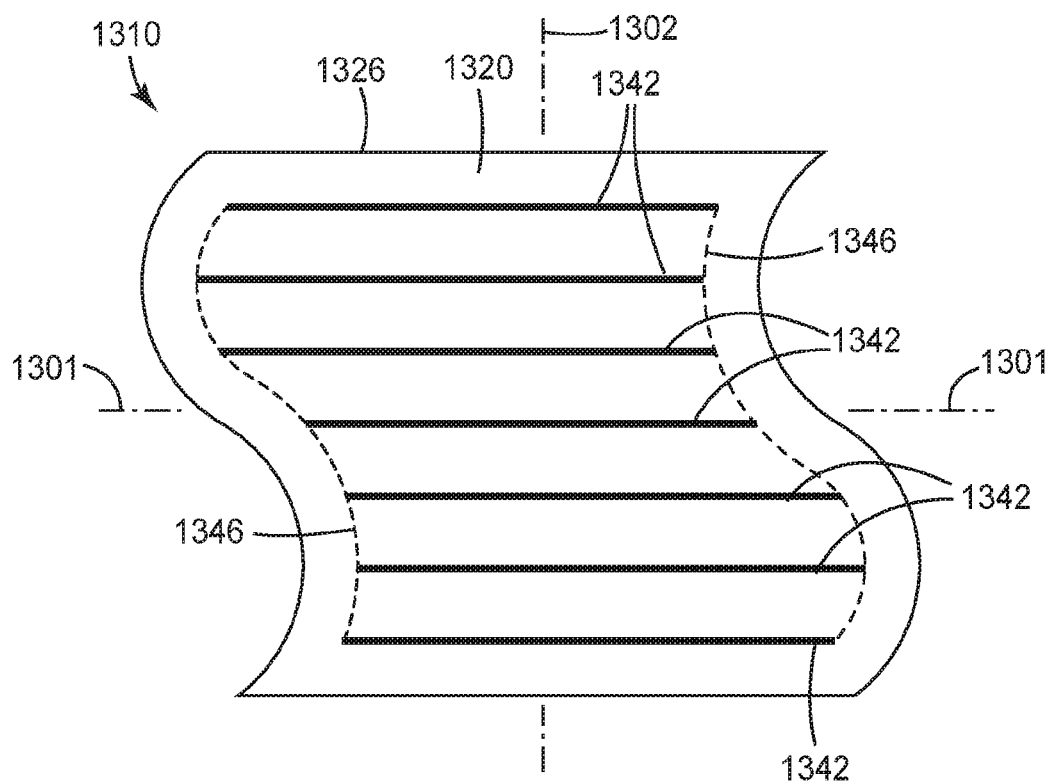
FIG. 19 is a perspective view of the medical dressing of FIG. 18 with the medical dressing being in a nonplanar configuration.

The first and second ends of the stiffening elements 1342 are spaced inwardly from the backing layer perimeter 1326. As a result, a stiffening system perimeter 1346 defined between the first ends of the stiffening elements 1342 and the second ends of the stiffening elements 1342 is also spaced inwardly from the backing layer perimeter 1326. Medical dressing 1310 in FIGS. 18-19 shows the stiffening system perimeter 1346 defined by the outermost stiffening elements 1342 (i.e., the stiffening elements 1342 on the top and bottom of the medical dressing 1310 as in FIG. 18) as well as the broken lines extending between the first ends of stiffening elements 1342 on one end and the broken lines extending between the second ends of stiffening elements 1342 at the opposite end of the stiffening elements 1342.

The stiffening system formed by stiffening elements 1342 on medical dressing 1310 defines a stiffening axis 1301. The longitudinal axes defined by the stiffening elements 1342 of the stiffening system provided on medical dressing 1310 are, in the embodiment, aligned with the stiffening axis 1301. In one or more embodiments, the alignment between stiffening axis 1301 and the longitudinal axes of the stiffening elements 1342 may be parallel, although some vary from a perfectly parallel relationship between the longitudinal axes defined by the stiffening elements 1342 and the stiffening axis 1301 (for example, ±15° or less) falls within the scope of alignment of the longitudinal axes of the stiffening elements 1342 with the stiffening axis 1301 of the stiffening system in medical dressings.

The widths of the stiffening elements 1342 are uniform along the length of each stiffening element 1342. In one or more embodiments, however, the width of one or more of the stiffening elements 1342 may vary along their length.

The transverse spacing between adjacent pairs of stiffening elements 1342 (where the transverse spacing is transverse to the stiffening axis 1301) is uniform when moving transverse to the stiffening axis 1301. In one or more embodiments, however, the transverse spacing between two or more adjacent pairs of stiffening elements 1342 may not be uniform when moving transverse to the stiffening axis 1301.

The stiffening elements 1342 extend in straight lines between their first and second ends. In one or more embodiments, one or more of the stiffening elements of a stiffening system defining a stiffening axis aligned with the longitudinal axes of the stiffening elements may not extend in a straight line between its first and second ends.

A stiffening system including a plurality of aligned stiffening elements such as stiffening elements 1342 that define a stiffening axis such as stiffening axis 1301 may, in one or more embodiments, provide a medical dressing that is more flexible in some directions and less flexible in other directions. Furthermore, stretching of a backing layer of such a medical dressing along the stiffening axis defined by the stiffening system may be limited, while stretching the backing layer in directions not aligned with the stiffening axis may be significantly less limited.

One example of these variations is in FIG. 19, where medical dressing 1310 is capable of being bent or flexed in directions around the stiffening axis 1301 but flexing or bending of the medical dressing 1310 in a direction transverse to the stiffening axis (for example, around transverse axis 1302) is limited by the stiffening elements 1342 of the stiffening system on medical dressing 1310.

The variations described herein with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.) may be provided in connection with stiffening systems having multiple stiffening elements extending along longitudinal axes that are aligned with a stiffening axis as in, for example, FIGS. 18-19.

Figure 20:
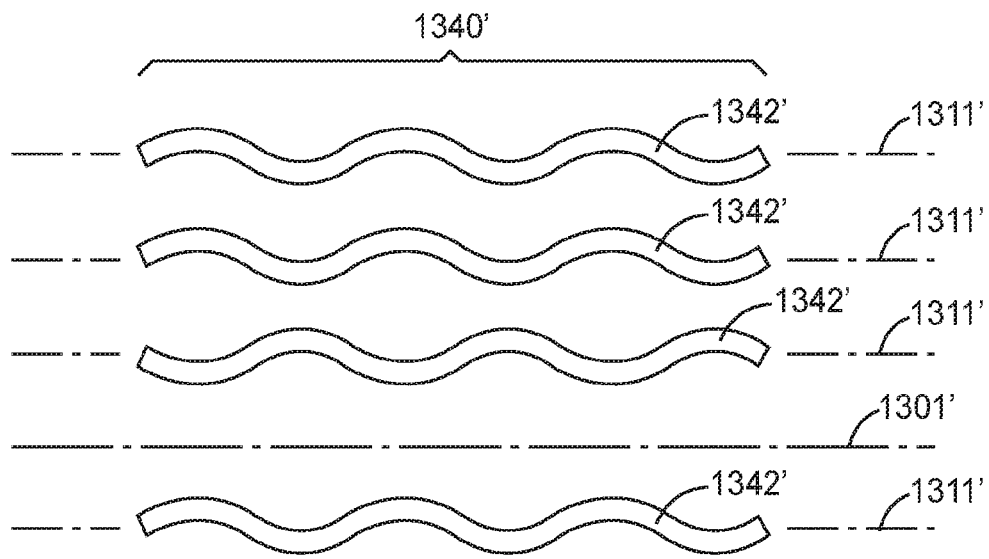
FIGS. 20-21 depict embodiments of stiffening systems that can define a stiffening axis using a plurality of stiffening elements extending along longitudinal axes.
Figure 21:
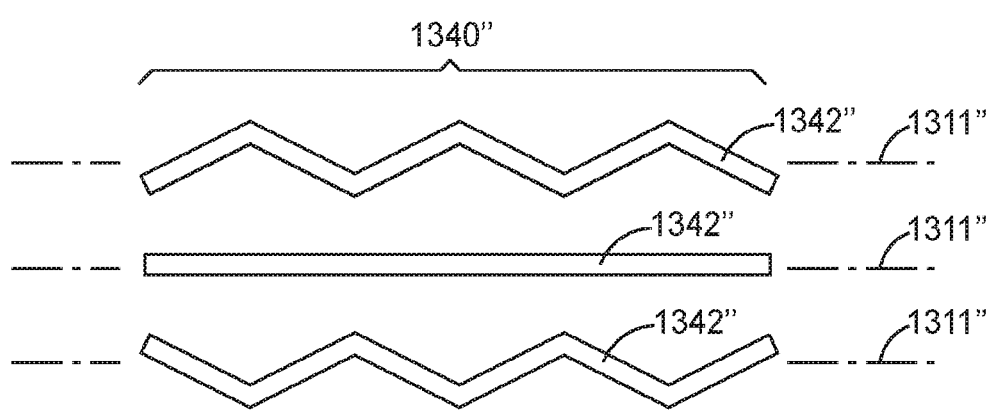

FIGS. 20-21 depict embodiments of stiffening systems that define a stiffening axis using a plurality of stiffening elements in which each of the stiffening elements defines a longitudinal axis aligned with the stiffening axis of the stiffening system.

FIG. 20 depicts stiffening system 1340' including stiffening elements 1342' each of which defines a longitudinal axis 1311'. The stiffening system 1340' defines a stiffening axis 1301', with each of the longitudinal axes 1311' being aligned with the stiffening axis 1301'.

One difference between the stiffening system 1340' including stiffening elements 1342' and the stiffening system on medical dressing 1310 in FIGS. 18-19 is that the stiffening elements 1342' do not extend in straight lines between their first and second ends. Each of the stiffening elements 1342' extends along a sinusoidal path aligned with the respective longitudinal axis for the stiffening element. In one or more variations, the stiffening elements 1342' may extend along sinusoidal paths that are aligned with each other as in the two uppermost stiffening elements 1342'. In another variation, stiffening elements 1342' may be out of alignment, as seen, for example, with the two innermost stiffening elements 1342'.

FIG. 21 depicts stiffening system 1340" including stiffening elements 1342", each of which defines a longitudinal axis 1311". The stiffening system 1340" includes a mixture of both straight and non-straight stiffening elements 1342". In particular, the innermost or intermediate stiffening element 1342" is in the form of a straight line, while the two outermost stiffening elements 1342" are in the form of sawtooth lines. Many other variations in line shapes for stiffening elements that define longitudinal axes aligned with a stiffening axis of the stiffening system including those stiffening elements may be provided in one or more embodiments of stiffening systems.

The variations described herein with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.) may be provided in connection with stiffening systems having stiffening elements extending along longitudinal axes that are aligned with a stiffening axis as in, for example, FIGS. 20-21.

FIGS. 20-23 are top views of medical dressings including stiffening systems that define a stiffening axis using a plurality of stiffening elements in which each of the stiffening elements defines a longitudinal axis aligned with the stiffening axis of the stiffening system.

Figure 22:
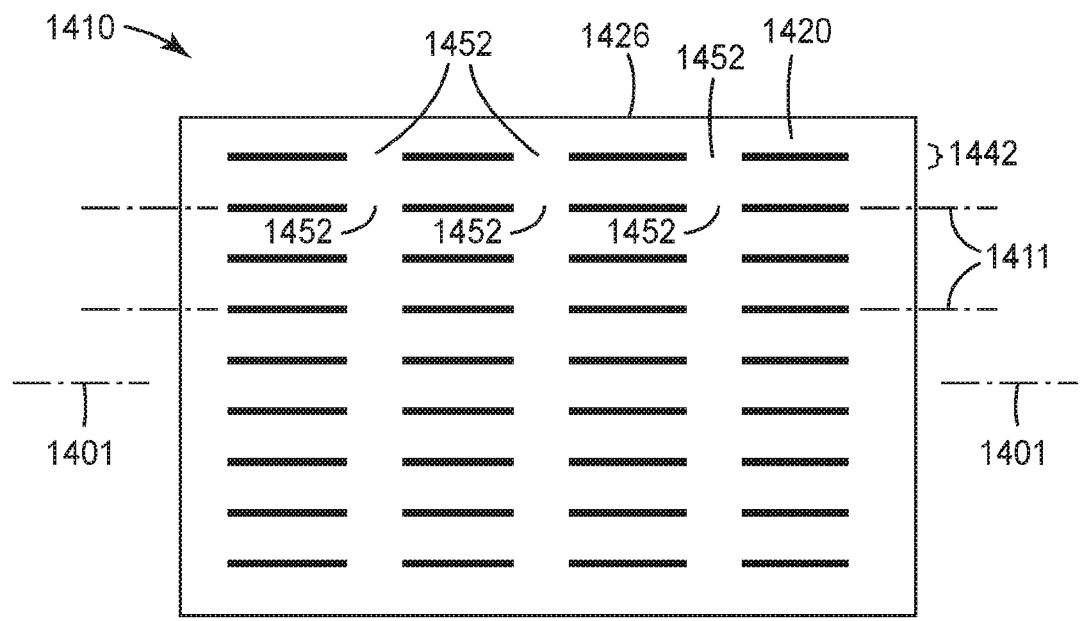
FIGS. 22-23 are top views of embodiments of medical dressings including stiffening systems defining a stiffening axis using a plurality of stiffening elements extending along longitudinal axes on a backing layer.
Figure 23:
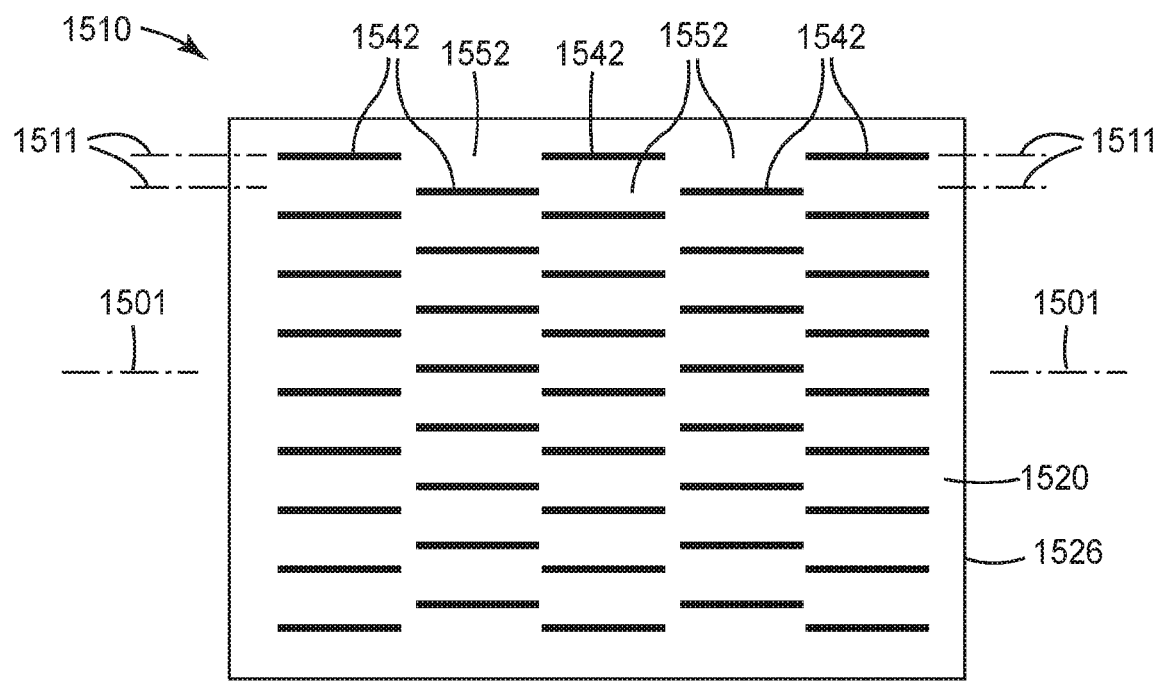

In many respects, the stiffening systems on medical dressings 1410 and 1510 of FIGS. 22-23 are similar to the stiffening systems in FIGS. 18-21 and the variations described with respect to those stiffening systems apply to the stiffening systems in FIGS. 22-23.

One difference is that the stiffening elements of the stiffening systems in FIGS. 18-21 are in the form of continuous stiffening elements, i.e., the stiffening elements extend continuously between their first and second ends. Stiffening elements 1442 and 1542 of medical dressings 1410 and 1510 include discrete segments separated from each other by gaps.

With respect to FIG. 22, the stiffening system on medical dressing 1410 includes a plurality of stiffening elements 1442, each of which includes segments separated by gaps 1452. The segments of each of the stiffening elements 1442 are, however, generally aligned along a longitudinal axis, for example, longitudinal axes 1411, depicted for some of the stiffening elements 1442 in FIG. 22. As discussed above, the longitudinal axes defined by the stiffening elements 1442 are aligned with a stiffening axis 1401 defined by the stiffening system as a whole.

With respect to FIG. 23, the stiffening system on medical dressing 1510 includes a plurality of stiffening elements 1542, each of which includes segments separated by gaps 1552. The segments of each of the stiffening elements 1542 are, however, generally aligned along a longitudinal axis, for example, longitudinal axes 1511, depicted for some of the stiffening elements 1542 in FIG. 23. As discussed above, the longitudinal axes defined by the stiffening elements 1542 are aligned with a stiffening axis 1501 defined by the stiffening system as a whole.

One feature in connection with the discontinuous stiffening elements 1442 including gaps 1452 of FIG. 22 is that the gaps 1452 of at least one adjacent pair of stiffening elements 1442 are aligned with each other in a direction transverse to the stiffening axis 1401. In contrast, the discontinuous stiffening elements 1542 including gaps 1552 of FIG. 23 are arranged such that the gaps 1552 of at least one adjacent pair of stiffening elements 1542 are not aligned or are offset with each other in a direction transverse to the stiffening axis 1501.

One or more embodiments of medical dressings including stiffening systems may include a combination of both aligned and misaligned gaps in stiffening systems including stiffening elements that define a stiffening axis as discussed in connection with FIGS. 18-23.

Further, alignment or misalignment of the gaps of discontinuous stiffening elements may, as discussed herein, affect the flexibility of a backing layer to which the stiffening system is fixedly attached.

Figure 24:
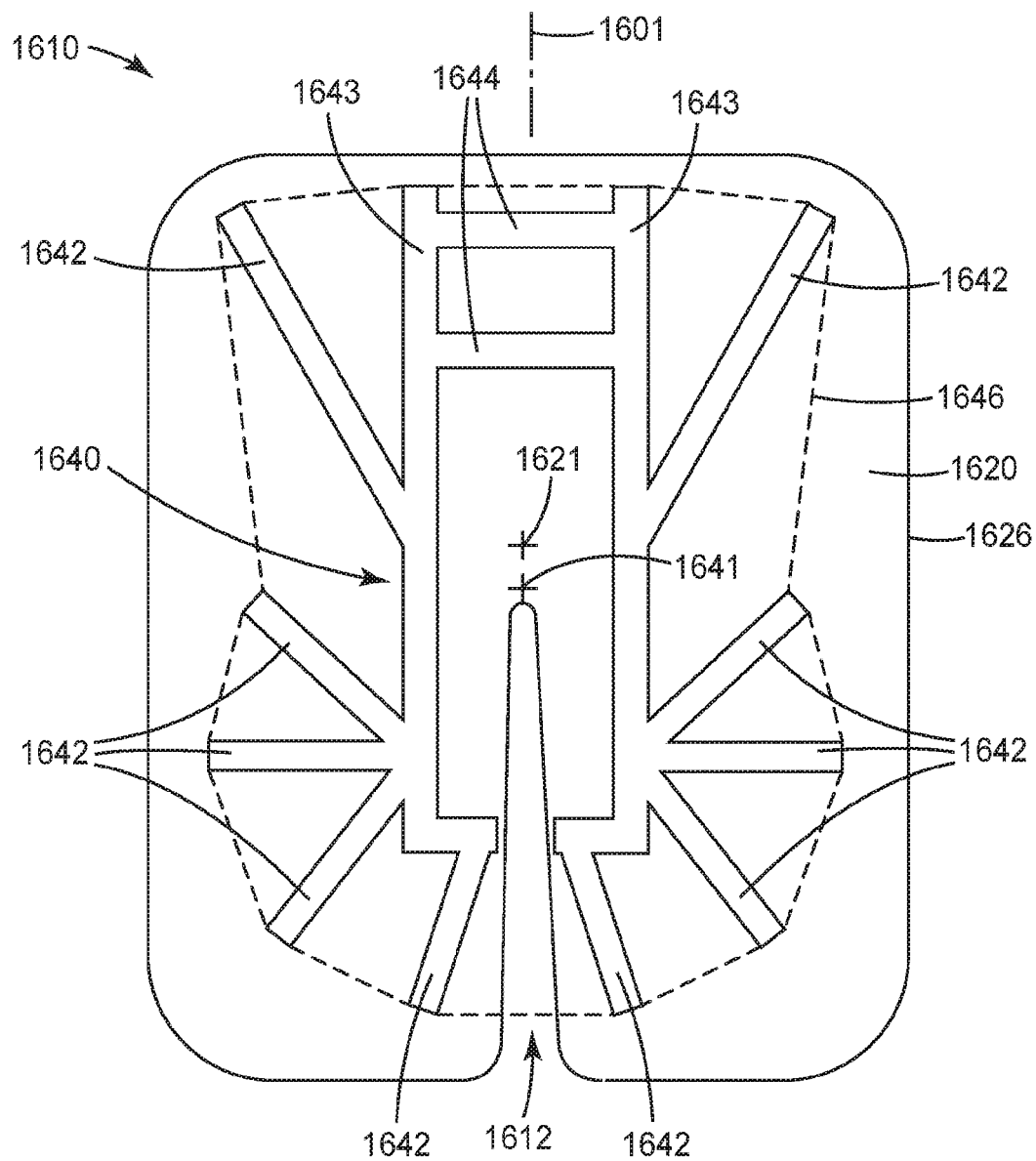
FIG. 24 depicts an embodiment of a medical dressing including a stiffening system designed to stabilize a catheter or other device.
Figure 25:
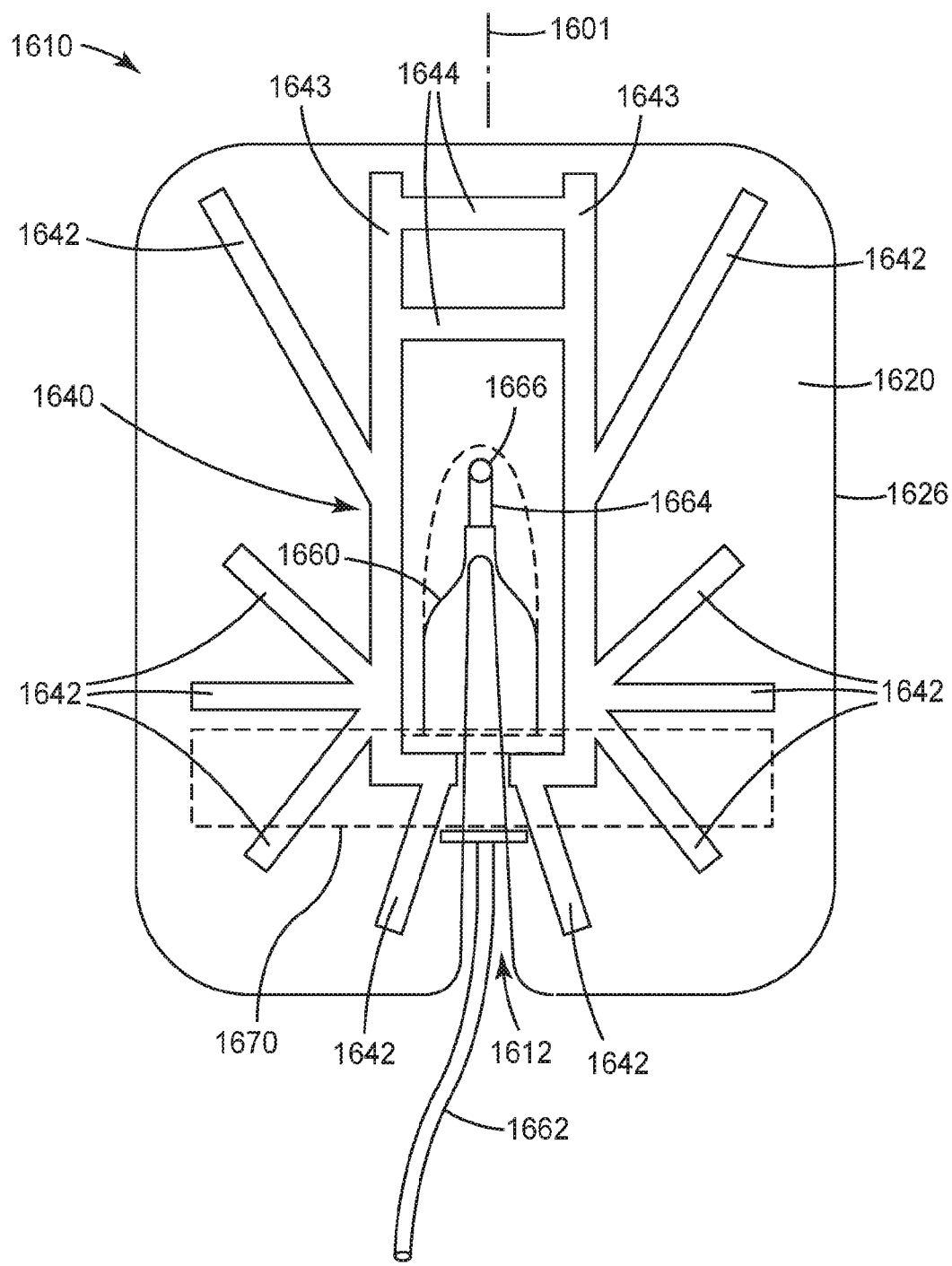
FIG. 25 depicts the medical dressing of FIG. 24 in position over a catheter.

Another embodiment of a medical dressing 1610 is in FIGS. 24-25. The medical dressing 1610 is depicted alone in FIG. 24 and in position over a catheter hub in FIG. 25. With reference to FIG. 24, the medical dressing 1610 includes a backing layer 1620 having a backing layer perimeter 1626. The medical dressing 1610 includes a slot 1612 extending inwardly towards a geometric center 1621 of the backing layer 1620 to assist with placement of the medical dressing 1610 over a catheter hub at an insertion site.

The embodiment of medical dressing 1610 includes a stiffening system 1640 used to provide support to the backing layer 1620 as discussed herein with respect to other embodiments of medical dressings. The stiffening system 1640 is bilaterally symmetric and defines a stiffening system perimeter 1646 disposed at the second ends of stiffening elements and a center 1641 disposed within that stiffening system perimeter. As discussed in connection with other embodiments of stiffening systems described herein, the stiffening system perimeter 1646 can be described as the area of the backing layer 1620 that is supported by the stiffening system, with the stiffening system perimeter 1646 being defined by lines extending between adjacent second ends of stiffening elements 1642, 1643 forming the stiffening system 1640.

The stiffening system 1640 in FIGS. 24-25 include some features common to many of the stiffening systems described herein. For example, stiffening system 1640 includes outwardly extending stiffening elements 1642. Outwardly extending stiffening elements 1642 may be described as extending generally outward and away from stiffening axis 1601 of the stiffening system 1640 and towards the backing layer perimeter 1626.

The embodiment of stiffening system 1640 also includes stiffening elements 1643 that are aligned with and that assist in defining a stiffening axis 1601 in a manner similar to that discussed above in connection with the stiffening systems in FIGS. 18-23. In that respect, the stiffening system 1640 may be considered to be a hybrid of the stiffening systems in, for example, FIGS. 1-2, 4-11, and 18-23.

Stiffening elements 1643 are, themselves, bridged by stiffening elements 1644 extending between stiffening elements 1643 to form what may be described as a ladder structure as a part of the stiffening system 1640.

As noted in FIG. 24, the geometric center 1621 of backing layer 1620 is not coincident with the center 1641 of the stiffening system 1640. As discussed elsewhere herein, in some embodiments of medical dressings those two centers may be coincident with each other. However, in other embodiments such as, for example, medical dressing 1610, the center of the backing layer 1620 may not be coincident with the center of the stiffening system 1640.

The variations described herein with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.) may be provided in connection with hybrid stiffening systems such as, for example, stiffening system 1640.

The medical dressing 1610 is depicted as being positioned over a catheter hub 1660 in FIG. 25. The catheter slot 1612 in backing layer 1620 facilitates placement of the dressing 1610 over the catheter hub and allows for tubing 1662 to pass out of the catheter hub 1660. A catheter 1664 is shown as extending from the catheter hub 1662 an insertion site 1666 located beneath the backing layer 1620 of medical dressing 1610.

The various features of the stiffening system 1640 serve to limit stretching of the backing layer 1620 and, therefore, also assist in maintaining position of the catheter hub 1660 and its related components relative to the insertion site 1666. Although not required, a secondary adhesive support 1670 (for example, adhesive tape, etc.) may be provided over the catheter hub 1660 and secured to the surface of the backing layer 1620 facing away from the patient to further assist in fixing the catheter hub 1660 relative to the insertion site 1666.

In one or more embodiments of medical dressings designed to secure a catheter hub relative to an insertion site, the stiffening system provided on such medical dressings may, in addition to limiting stretch of a backing layer, potentially provide lift to selected regions of the skin located within the area occupied by the stiffening system. For example, with respect to stiffening system 1640, the arrangement of stiffening elements 1643 and 1644 on opposing sides of the insertion site may provide lift to the skin and underlying tissue proximate the insertion site 1666. In one or more embodiments, that additional lift provided by the stiffening system of the medical dressing may reduce the likelihood of veins or other vascular structure directly beneath those portions of the skin from collapsing. This phenomenon may, for example, be similar to the effect that adhesive nasal dilators designed to be adhered to the outside of a nose to open or at least prevent closure of underlying nasal passages such as those described in, for example, U.S. Pat. No. 5,533,503 (Doubek et al.); U.S. Pat. No. 5,546,929 (Muchin), etc.

One or more embodiments of medical dressings may be used in one or more embodiments of methods of improving patency of blood vessels proximate a catheter insertion site. For example, the methods may include positioning a medical dressing comprising a stiffening system (including outwardly extending stiffening elements, stiffening elements in the form of nested rings, aligned stiffening elements defining one or more stiffening axes, and combinations of one or more thereof) over a catheter insertion site; and adhesively attaching the medical dressing to skin proximate the insertion site such that a pair of stiffening elements of the stiffening system are located on opposite sides of the catheter insertion site.

While stiffening system 1640 of FIGS. 24-25 represents one example of a hybrid stiffening system incorporating both linear stiffening elements 1643 and outwardly extending stiffening elements 1642, another example of a hybrid stiffening system is seen in connection with the stiffening system 840 in FIG. 11. Stiffening system 840 can, in one or more embodiments, be described as incorporating both outwardly (for example, radially) extending stiffening elements 842 and nested or concentric ring-shaped stiffening elements 843 and 850. In other embodiments, the nested or concentric stiffening elements may only be found between one or more selected pairs of outwardly (for example, radially) extending stiffening elements of a stiffening system. Although not specifically described, many other hybrid stiffening systems incorporating different types of stiffening elements into stiffening systems attached to medical dressing may also be provided and should not be limited to the embodiments of hybrid stiffening systems specifically described herein.

Although many of embodiments of medical dressing described herein are discussed in terms of geometric centers and stiffening system perimeters/areas located within backing layer perimeters, the medical dressing described herein may be described as including stiffening systems that are located or contained with a selected interior region or a central region of the backing layer.

For example, the stiffening system on backing layer 20 of medical dressing 10 of FIG. 1 may be described as being contained within a selected interior region 46, the selected interior region 46 being spaced inward from the perimeter 26 of the backing layer 20. The stiffening system includes elongated stiffening elements 42 contained within the selected interior region 46. Each stiffening element 42 extends from a first end to a second end, with the first end of each stiffening element 42 located closer to a center 41 of the selected interior region 46 than the second end. Further, the second end of each stiffening element 42 is located closer to the perimeter 26 of the backing layer 20 than the first end. In addition, the second end of each stiffening element 42 is spaced inward from the perimeter 26 of the backing layer 20 and is completely surrounded by the backing layer 20.

In another example, the stiffening system on backing layer 920 of medical dressing 910 of FIG. 14 may be described as being contained within a selected interior region 946 of the backing layer 920, the selected interior region 946 being spaced inward from the perimeter 926 of the backing layer 920. The stiffening system includes a plurality of nested stiffening elements 942, wherein each stiffening element 942 defines a ring located within the selected interior region 946. The outermost stiffening element 942 is spaced inward from the perimeter 926 of the backing layer 920 and is completely surrounded by the backing layer 920.

In still another example, the stiffening system depicted on backing layer 1320 of medical dressing 1310 of FIG. 18 may be described as being contained within a selected interior region 1346 of the backing layer 1320, the selected interior region 1346 being spaced inward from the perimeter 1326 of the backing layer 1320. The stiffening system defines a stiffening axis 1301 extending across the selected interior region 1346 in a selected direction. The stiffening system includes a plurality of stiffening elements 1342, with each stiffening element 1342 including a first end and a second end defining a length along a longitudinal axis extending through the first and second ends and a width measure transverse to the longitudinal axis. The first and second ends of each stiffening element 1342 are located within the selected interior region 1346 and spaced inwardly from the perimeter 1326 of the backing layer 1320 such that the first and second ends are completely surrounded by the backing layer 1320. Further, the longitudinal axis of each stiffening element 1342 is aligned with the stiffening axis 1301 of the stiffening system.

One or more embodiments of medical dressing described herein may include selected interior regions containing stiffening systems that are not centered on the backing layer.

Still another feature of one or more embodiments of medical dressings including stiffening systems contained within a selected interior region of a backing layer is that the selected interior region may occupy 95% or less, 85% or less, 75% or less, or even 65% or less of the backing area of the backing layer.

The stiffening elements of the stiffening systems do not, however, completely occupy significant portions of the backing layer as compared to conventional approaches to limiting stretching of elastic backing layers of medical dressings. In contrast, the selected interior regions containing the stiffening elements of stiffening systems may, in one or more embodiments, be described as occupying 50% or less, 40% or less, 30% or less, 20% or less, 10% or less, or even 5% or less of the backing layer.

The selected interior regions containing the stiffening elements of stiffening systems may, in one or more embodiments, be described in terms of the minimum amount of the area occupied by the stiffening elements of the stiffening system. In one or more embodiments, the stiffening elements of stiffening systems may be described as occupying 2% or more, 4% or more, 6% or more, 8% or more, or even 10% or more of the selected interior region containing the stiffening system.

Figure 26A:
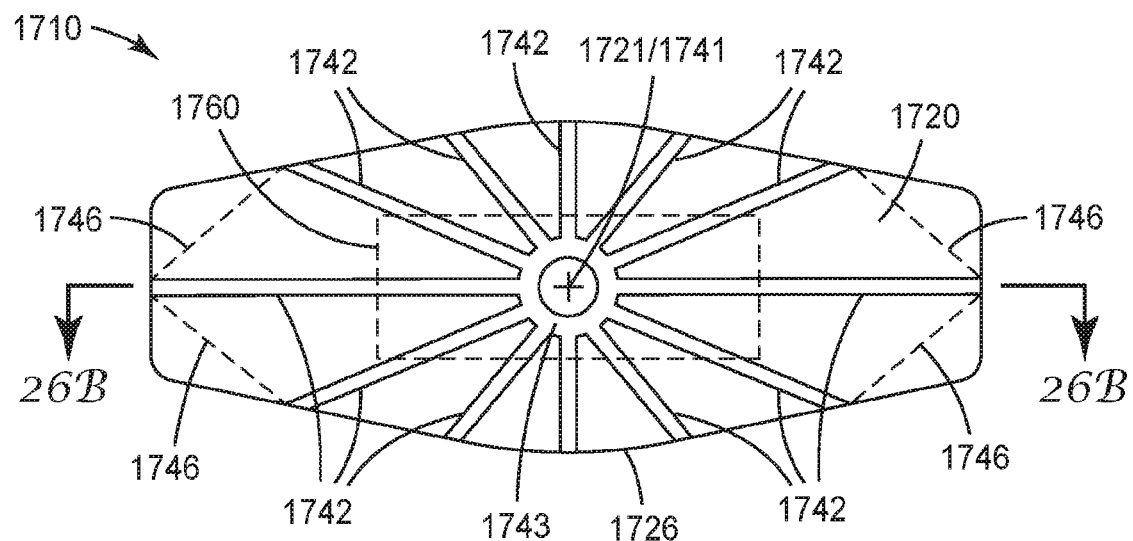
FIG. 26A depicts an embodiment of a medical dressing including a stiffening system, with the medical dressing including a pad located thereon.
Figure 26B:
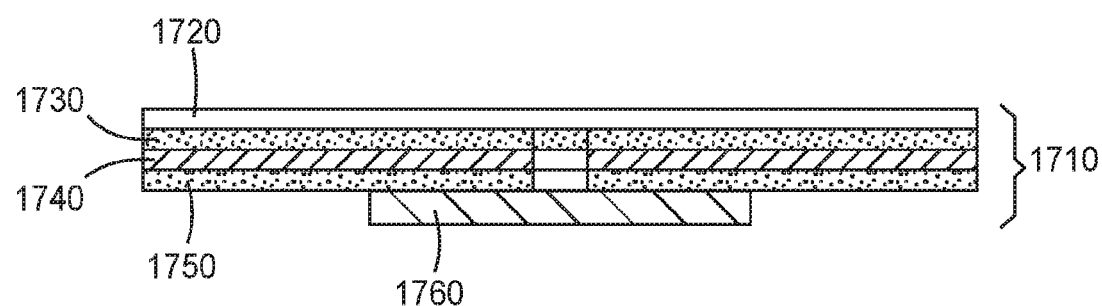
FIG. 26B is a cross-sectional view of the medical dressing of FIG. 26A taken along line 26B-26B in FIG. 26A.

Another embodiment of a medical dressing including a stiffening system is in FIGS. 26A-26B. The medical dressing 1710 includes a backing layer 1720 having a perimeter 1726, as well as a stiffening system including stiffening elements 1742 extending outwardly from a central support 1743 towards the perimeter 1726 of the backing layer 1720. The stiffening system is contained within a selected region of the backing layer 1720, with the selected region being substantially contact transparent.

The outermost or second ends of the stiffening elements 1742 can, define a stiffening system perimeter (also referred to as a region perimeter) 1746. The medical dressing 1710, portions of the stiffening system/region perimeter 1746 are shown as being spaced inwardly from the perimeter 1726 of the backing layer 1720, while other portions of the stiffening system/region perimeter 1746 are essentially collinear with the perimeter 1726 of the backing layer 1720. In such an embodiment in which at least a portion of the stiffening system/region perimeter 1746 is spaced inwardly from the perimeter 1726 of the backing layer 1720, the selected region in which the stiffening system is contained may be described as a selected interior region.

Each of the stiffening elements 1742 extends from a first end to a second end. The first ends of the stiffening elements 1742 are located closer to a center 1741 of the stiffening system than the second ends of the stiffening elements 1742. Further, the second ends of each stiffening element 1742 are located closer to the stiffening system/region perimeter 1746 than the first ends. The backing layer 1720 defines a geometric center 1721 that is coincident with the geometric center 1741 of the stiffening system 1740, although, such coincidence between centers is not required in medical dressings.

The medical dressing 1710 also includes a pad 1760 located on the medical dressing 1710. The pad 1760 may take any suitable form used in connection with medical dressings. For example, the pad 1760 may provide absorbency, antibacterial activity, medicament delivery, etc. In one or more embodiments, a pad used on a medical dressing may be constructed of any suitable material or combination of materials that provides the desired functionality, for example, woven materials, nonwoven materials, foams, gels, etc. Further, although the stiffening system 1740 is, in the embodiment, as being located between the pad 1760 and the backing layer 1720 (see, for example, FIG. 26B), one or more embodiments of medical dressings that include pads and stiffening systems may include a stiffening system on the opposite side of the backing layer such that the backing layer 1720 is located between the stiffening system 1740 and the pad 1760. The pads used in one or more embodiments of medical dressings may be affixed to the medical dressing by any suitable technique or combination of techniques known to be used in combination with medical dressings.

Although medical dressings including pads and stiffening systems may result in a medical dressing that is not, as a whole, substantially contact transparent within the selected region containing the stiffening system, the medical dressing may be described as remaining substantially contact transparent in the portion or portions of the selected region that are outside of the pad but that remain within the selected region containing the stiffening system. In the embodiment of medical dressing 1710, the portion of the selected region bounded by the region perimeter 1746 that is outside of the pad 1760 will remain substantially contact transparent despite the presence of the stiffening system (although as also described herein, the stiffening system itself may be opaque, colored, etc.).

The variations with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.) may be provided in connection with stiffening systems such as stiffening system 1740.

Stiffening systems may be incorporated into existing medical dressings having backing layers that exhibit elasticity and for which support is desired without unduly compromising the contact transparency of portions of the medical dressings. One embodiment of a medical dressing 1810 designed for catheter securement is in FIG. 27. Examples of similar dressings may be found in International Publication No. WO 2019/073326 A1 (Heinecke et al.).

Figure 27:
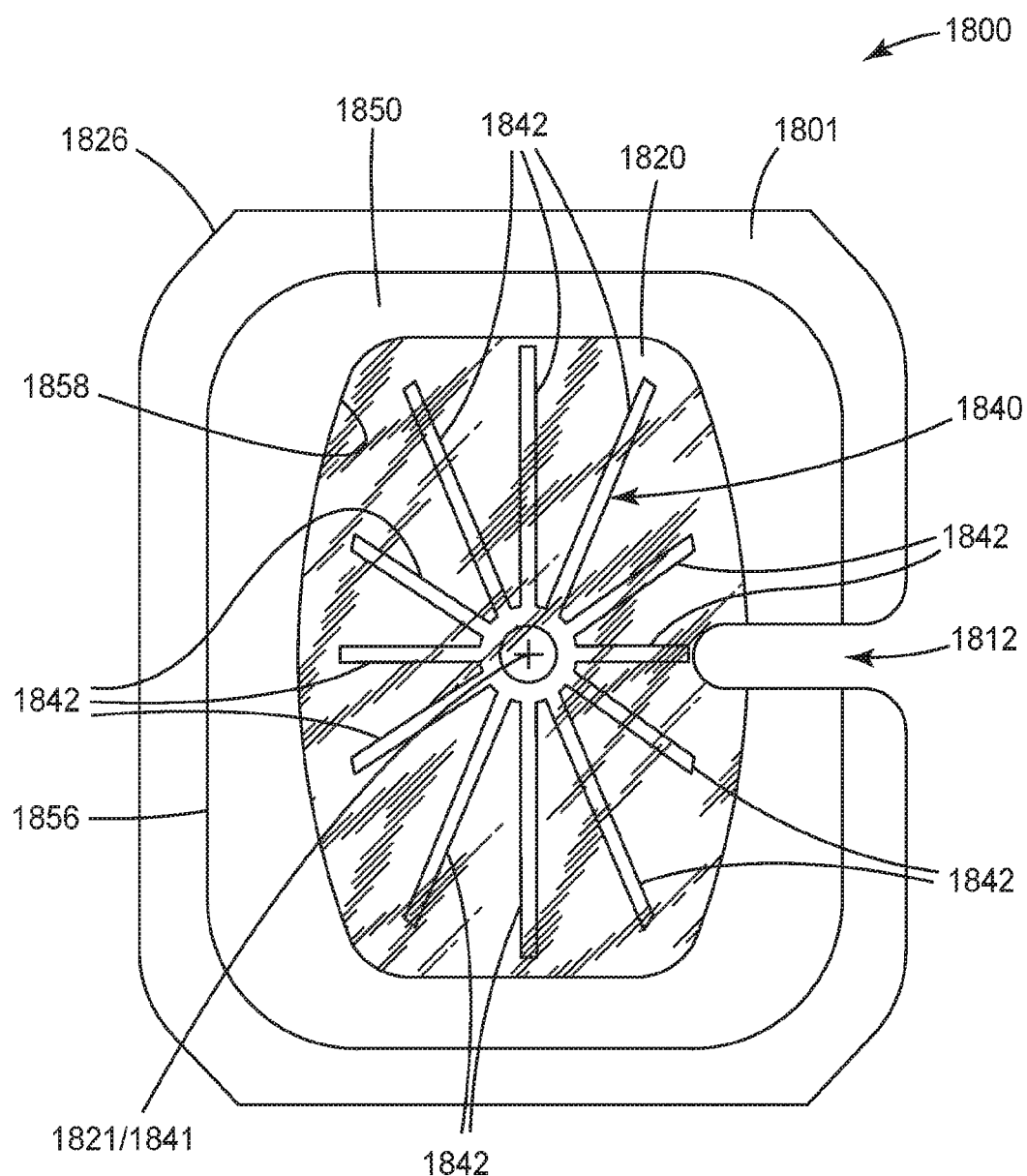
FIGS. 27-29 depict embodiments of medical dressings including a stiffening system.

Medical dressing 1810 as in FIG. 27 includes a backing layer 1820 having a backing layer perimeter 1826. A tubing slot 1812 is formed in the medical dressing 1800, with the tubing slot 1812 being configured to, for example, stabilize a catheter or other tubing on the skin of a patient. Support material 1850 is provided on the backing layer 1820, with the support material 1850 including an outer perimeter 1856 and an inner perimeter 1858 such that the support material 1850 defines a window formed by the backing layer 1820 (and any adhesive located thereon) that is contact transparent to allow viewing through the backing layer 1820 in the window. Support material 1850 also defines a border or perimeter 1801 between the outer perimeter 1856 of the support material and the perimeter 1826 of the backing layer 1820 that may improve conformability of the medical dressing 1810 around its perimeter.

Support material 1850 may, in one or more embodiments, be constructed of one or more layers of material that prevent the viewing of underlying tissue and/or devices located beneath the support material 1850. In one or more embodiments, the support material may be in the form of woven materials, nonwoven materials, films, etc. that occupy all of the area of the backing layer on which the support material is located, and which are not selected for their transparency or translucency.

In the embodiment, medical dressing 1800 further includes a stiffening system 1840 including stiffening elements 1842. Stiffening system 1840 may be provided to stabilize the backing layer 1820 within the window of the medical dressing 1800. The stiffening system 1840 may define a geometric center 1841 that is coincident with a geometric center 1821 of the window formed in the medical dressing 1800, although such coincidence is not required.

The variations with respect to stiffening systems having outwardly extending stiffening elements as described in connection with, for example, FIGS. 1-2 and 4-11 (for example, elasticity, elongation at break, optical properties (for example transparency, opacity, etc.), area occupied by the stiffening system, etc.) may be provided in connection with stiffening systems used in medical dressings that include other support materials such as, for example, support material 1850 such as stiffening system 1840.

Figure 28:
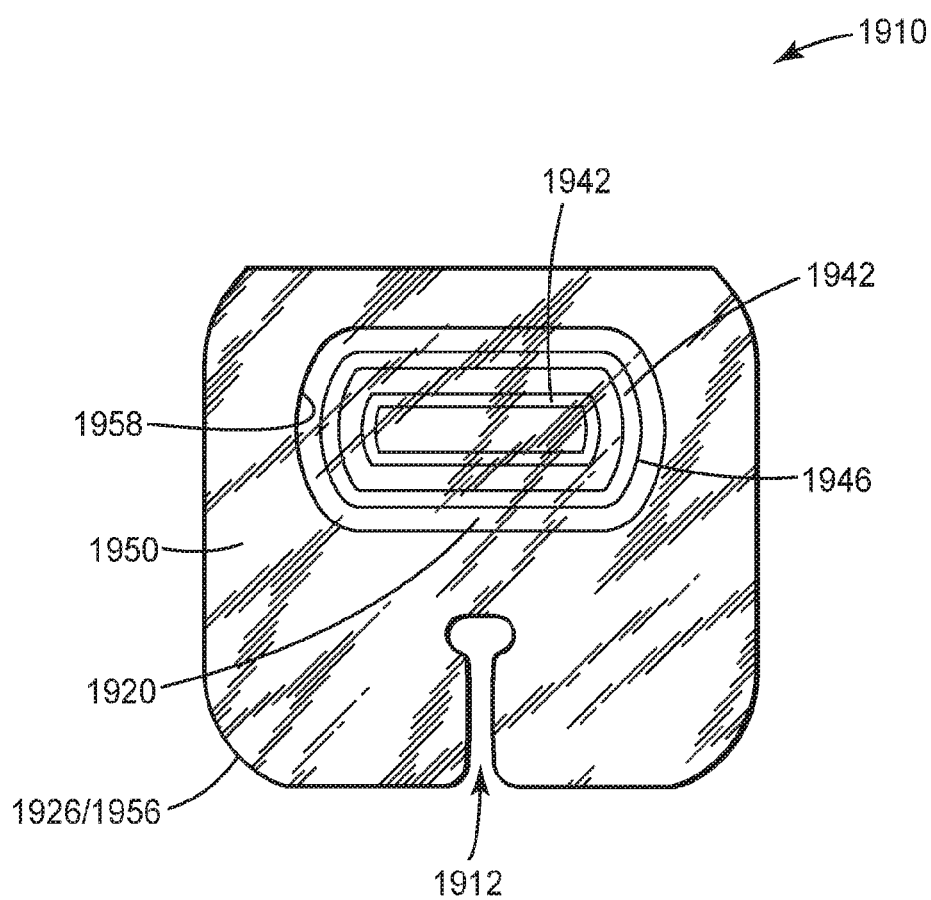

Medical dressing 1910 in FIG. 28 provides another embodiment of a medical dressing 1910 that includes support material 1950 on a backing layer 1920 to provide support to the backing layer as described above in connection with medical dressing 1800 in FIG. 27. Medical dressing 1910 also includes a tubing slot 1912 and support material 1950 and backing layer 1920 both define outer perimeters 1926/1956 of the medical dressing 1910.

Support material 1950 includes an interior perimeter 1958 that defines a window in which the backing layer 1920 is exposed and in which the medical dressing 1910 is contact transparent to allow viewing of underlying tissue/skin and/or devices on which the medical dressing 1910 is positioned. Another embodiment of a stiffening system including stiffening elements 1942 is in the window formed by the interior perimeter 1958 of support material 1950. The stiffening elements 1942 are in the form of nested or concentric rings with respect to other embodiments of stiffening systems on medical dressings. The stiffening elements 1942 define a stiffening system/region perimeter 1946 that is defined by the outermost stiffening element 1942 in the embodiment.

All of the variations described herein with respect to stiffening systems having outwardly extending stiffening elements, for example, FIGS. 1-2 and 4-11 (for example, elasticity, elongation at break, optical properties (for example transparency, opacity, etc.), area occupied by the stiffening system, etc.), as well as stiffening elements in the form of concentric rings as described in FIGS. 14-15 (for example, radial spacing between adjacent rings, variations in ring width, etc.) may be provided in connection with stiffening systems used in windows formed in medical dressings as in FIG. 28.

Figure 29:
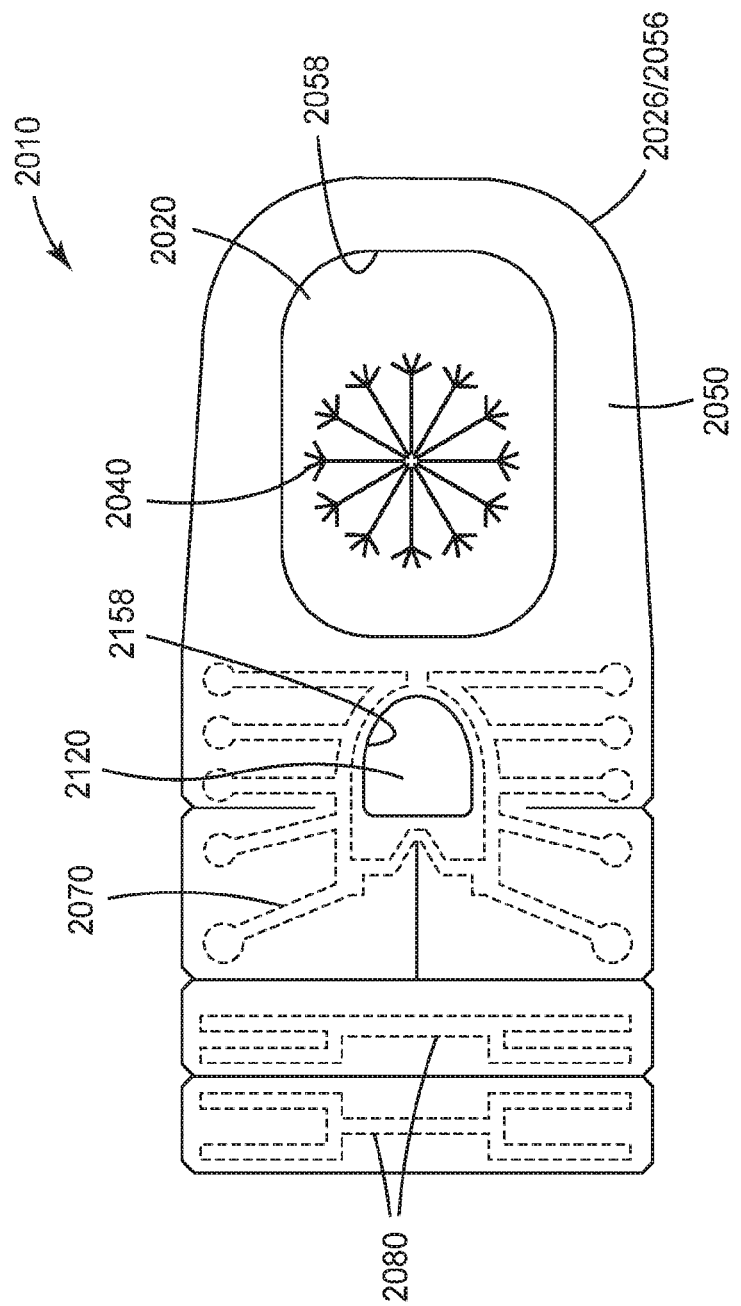

Another embodiment of a stiffening system incorporated into an existing medical dressing is in FIG. 29. The existing medical dressing may be described in, for example, U.S. Pat. No. 7,294,752 B1 (Propp). The medical dressing 2010 includes a backing layer 2020 defining a backing layer perimeter 2026. Medical dressing 2010 also includes support material 2050 having an inner perimeter 2058 defining a window in which the backing layer 2020 is exposed and is contact transparent to allow viewing through the backing layer 2020 in the window. Support material 2050 includes a perimeter 2056 in medical dressing 2010 that is essentially coextensive with the backing layer perimeter 2026.

One embodiment of a stiffening system 2040 is provided in the window formed by the inner perimeter 2058 of support material 2050 and is used to support the backing layer 2020 within the window.

Other features included in medical dressing 2010 are a second window 2120 exposing the backing layer 2020 by virtue of a second inner perimeter 2158 formed in support material 2050. Medical dressing 2010 further includes various support structures such as structure 2070 and structures 2080 that are located between the support material 2050 and the backing layer 2020. Unlike the stiffening systems described herein (see, for example, stiffening system 2040 in medical dressing 2010), however, support structures 2070 and 2080 are not located in any viewable window within medical dressing 2010.

Figure 30A:
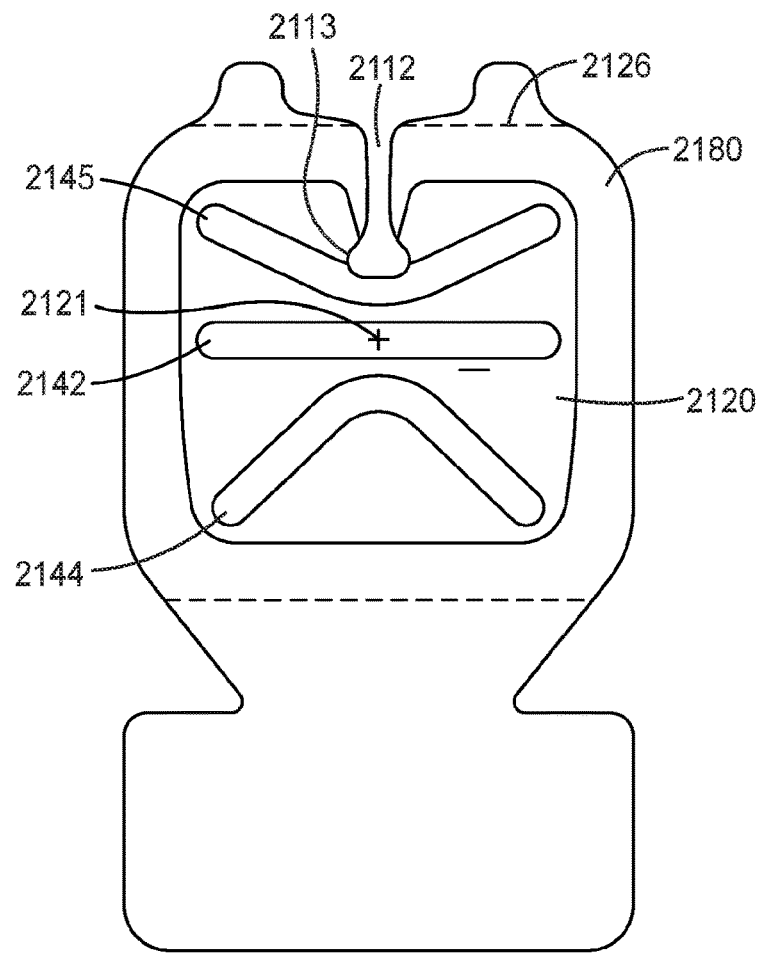

Medical dressing 2110 in FIGS. 30A and 3B provides another embodiment of a medical dressing 2110. FIG. 30A shows medical dressing 2110 supported by a removable carrier 2180 while FIG. 30B shows medical dressing 2110 after the removable carrier 2180 is removed.

Medical dressing 2110 includes a backing layer 2120 having a backing layer perimeter 2126. A tubing slot 2112 extends inwardly towards a geometric center 2121 of the backing layer 2120 to assist with placement of the medical dressing 2110 over a medical device to stabilize a catheter or other tubing on the skin of a patient. In the exemplary embodiment shown in FIGS. 30A and 30B, tubing slot 2112 has an enlarged closed end 2113 which is useful when the medical dressing is used with a medical device (not shown) that uses a large connection device, such as a luer lock style connection device, to attach tubing to the medical device.

Medical dressing 2110 further includes a stiffening system 2140 comprising at least one stiffening element to provide support to the backing layer 2120 as discussed herein with respect to other embodiments of medical dressings. The stiffening system 2140 defines a stiffening system perimeter 2146. Stiffening elements 2142, 2144, 2145 are disposed on backing layer 2120 generally transverse to the tubing slot 2112. The stiffening element 2142 is a linear element disposed in a direction transverse to tubing slot 2112 and stiffening elements 2144, 2145 are concave elements disposed on either side of stiffening element 2142 such that the first and second ends of stiffening elements 2144, 2145 extend away from stiffening element 2142. In the embodiment shown in FIGS. 30A and 30B, a portion of stiffening element 2145 is formed around the enlarged closed end 2113 of tubing slot 1812 to stabilize the tubing slot. The width of stiffening element 2145 is smaller in the area around the end of the tubing slot than at the ends of the stiffening member. In this design, the stiffening elements constrain elongation of the backing in a direction transverse to the tubing slot while allowing greater access in-line with the tubing slot.

Figure 30B:
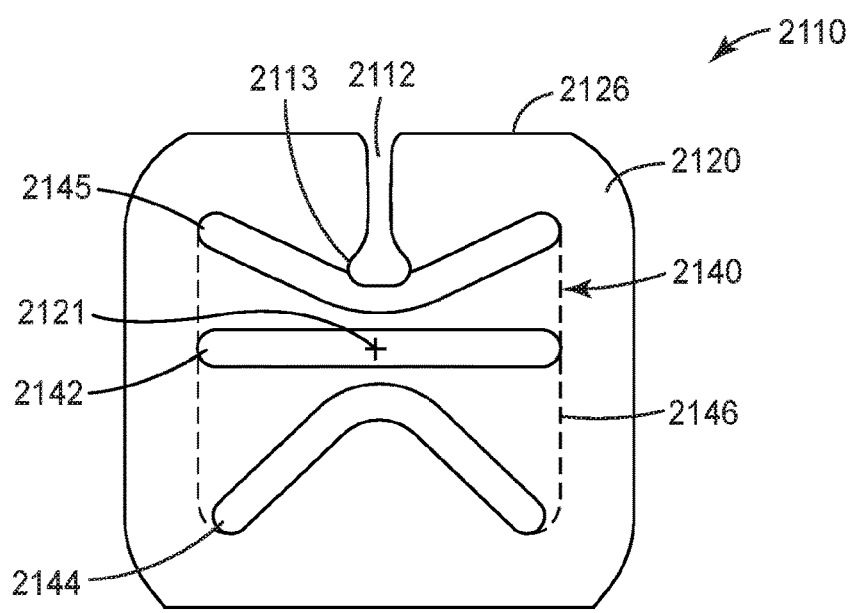

Medical dressing 2210, 2210', 2210", 2210''' in FIGS. 31A-31D show modifications of the stiffening system design of medical dressing of a medical dressing 2110 shown in FIG. 30B. Each of these medical dressings can be classified as having bilateral symmetry around an axis of symmetry 2215.

Figure 31A:
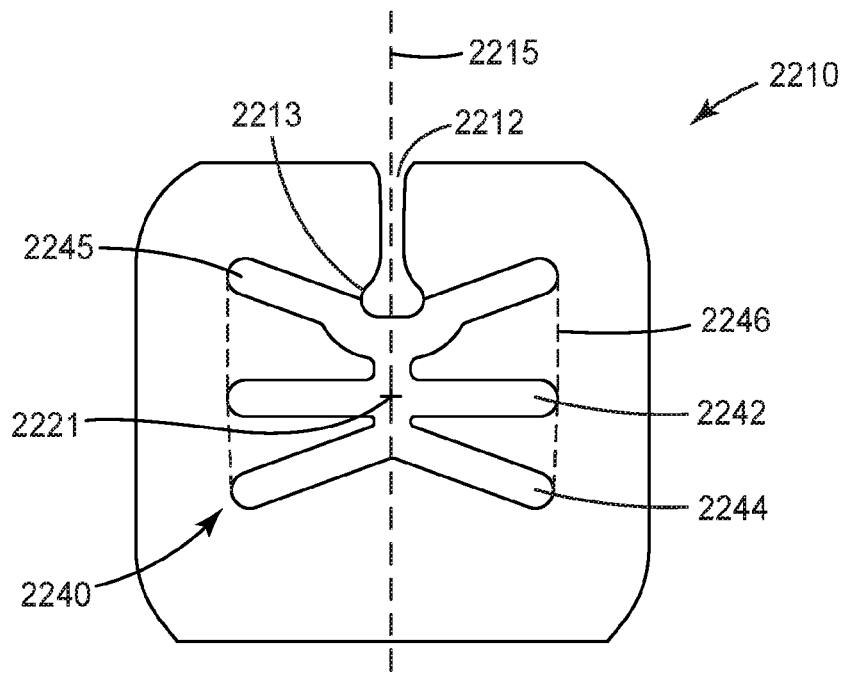
FIGS. 31A-31D depict embodiments of medical dressings including a stiffening system.

Medical dressing 2210, shown in FIG. 31A, includes a stiffening system 2240 having a plurality of stiffening elements to provide support to the backing layer 2220, wherein the stiffening system 2240 defines a stiffening system perimeter 2246. Stiffening elements 2242, 2244, 2245 are disposed on backing layer 2220 generally transverse to the tubing slot 2212 and are interconnected by central support or spine 2243. Central support 2243 constrains the inline elongation (i.e. in-line with tubing slot 2212) of backing layer 2220 when installed over a medical device more than the stiffening system of FIG. 30B. The stiffening element 2242 is a linear element disposed in a direction transverse to tubing slot 2212 and stiffening elements 2244, 2245 are concave elements disposed on either side of stiffening element 2242 such that the first and second ends of stiffening elements 2244, 2245 extend away from stiffening element 2242. In the exemplary embodiment shown in FIG. 31A, a portion of stiffening element 2245 is formed around the enlarged closed end 2213 of tubing slot 2212 to stabilize the tubing slot. In this exemplary embodiment, stiffening element has a constant width along its length.

Figure 31B:
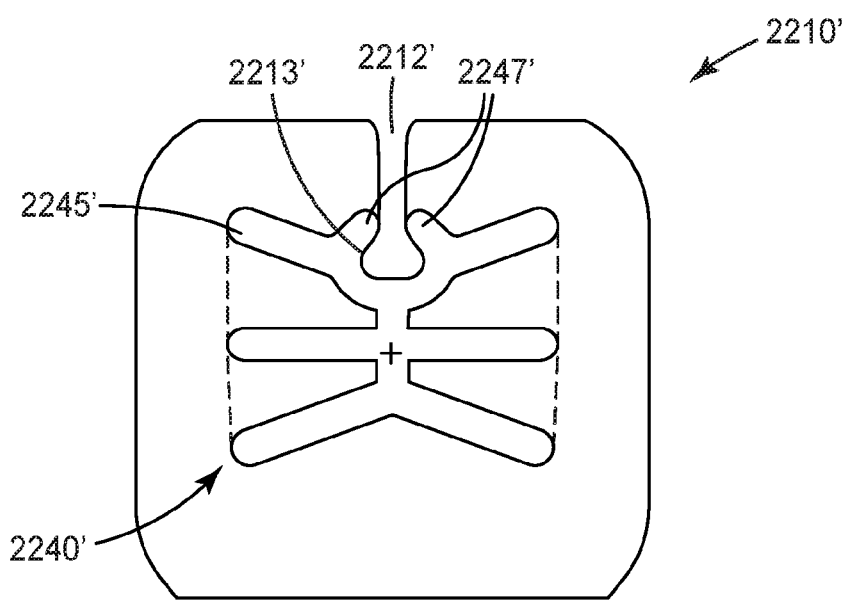

The stiffening system 2240' of medical dressing 2210' in FIG. 31B is substantially the same as stiffening system 2240 of medical dressing 2210, except as noted herein. Stiffening system 2240' further includes stiffening extensions 2247' extending from stiffening element 2245' around the enlarged closed end 2213' of tubing slot 2212' to stabilize the enlarged portion the tubing slot.

Figure 31C:
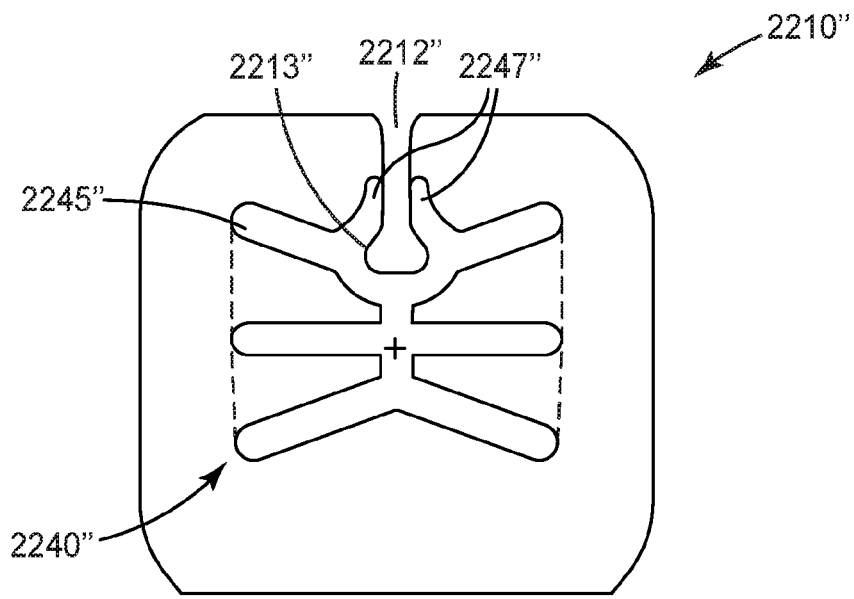

The stiffening system 2240" of medical dressing 2210" in FIG. 31C is also substantially the same as stiffening system 2240 of medical dressing 2210, except as noted herein. Stiffening system 2240" further includes stiffening extensions 2247" extending from stiffening element 2245" around the enlarged closed end 2213" and along a portion of the length of tubing slot 2212" to stabilize and stiffen the backing layer 2220" around tubing slot.

Figure 31D:
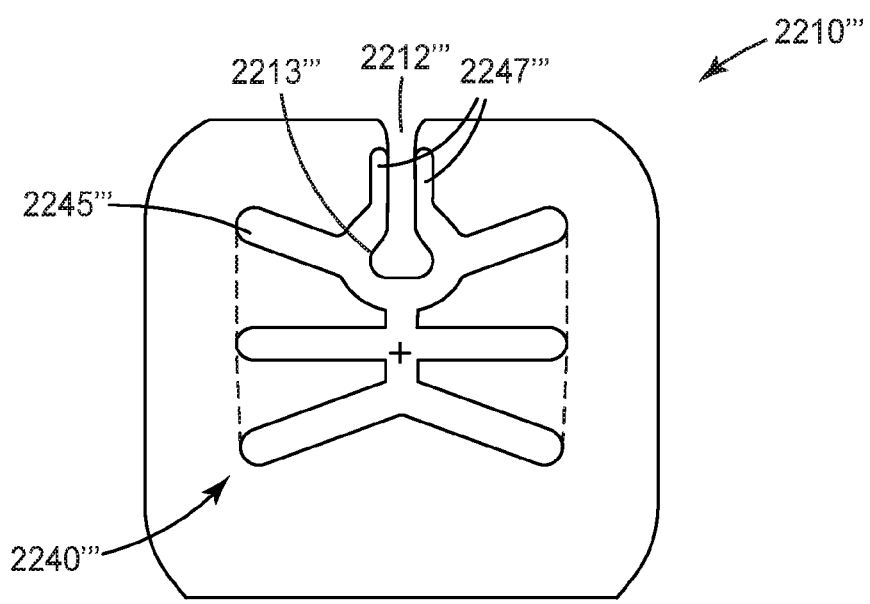

The stiffening system 2240''' of medical dressing 2210''' in FIG. 31D is also substantially the same as stiffening system 2240 of medical dressing 2210, except as noted herein. Stiffening system 2240''' further includes stiffening extensions 2247''' extending from stiffening element 2245''' around the enlarged closed end 2213''' and along the length of tubing slot 2212''' to stabilize and stiffen the backing layer 2220''' around tubing slot.

The degree of stiffening needed around the tubing slot may vary depending on the elastic properties of backing layer of the medical dressing, the size of the medical dressing, the size and the geometry of the medical device to be secured, as well as the installation location of the medical device on the patient's body. Providing the proper degree of stiffening can prevent movement or dislodgement of a medical device secured by the exemplary medical dressings described herein.

Figure 32A:
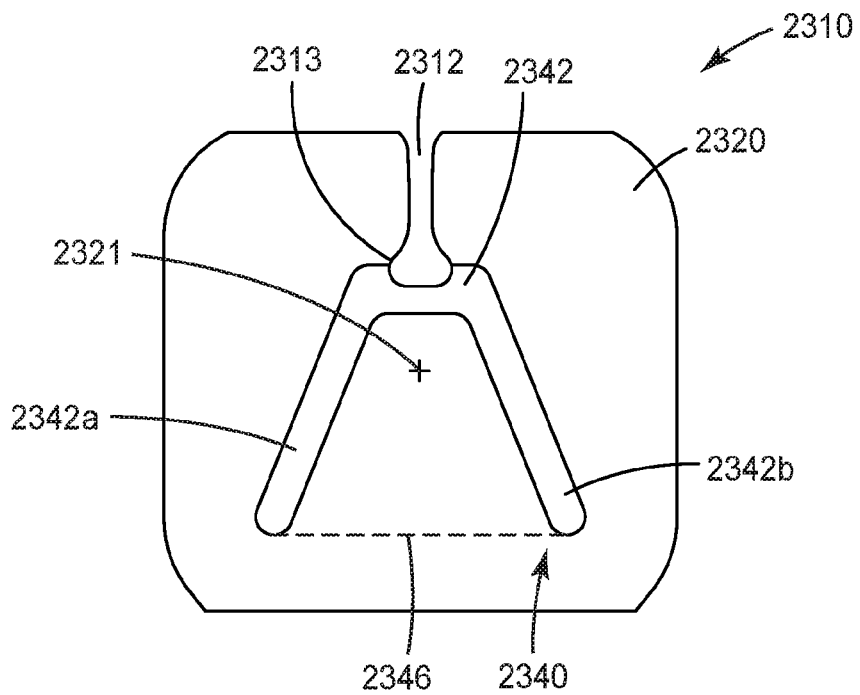
FIGS. 32A and 32B depict embodiments of medical dressings including a stiffening system.

FIG. 32A shows another embodiment of a medical dressing 2310 having a backing layer 2320 wherein the outside edge of the backing layer defines a backing layer perimeter. A tubing slot 2312 having an enlarged closed end 2313 extends inwardly towards a geometric center 2321 of the backing layer 2320, the tubing slot 2312 aids placement of the medical dressing 2310 over a medical device to stabilize a catheter or other tubing on the skin of a patient.

Medical dressing 2310 further includes a bilaterally symmetric stiffening system 2340 comprising a stiffening element 2342 to provide support to the backing layer 2320 as discussed herein with respect to other embodiments of medical dressings. The stiffening system 2340 defines a stiffening system perimeter 2346. Stiffening element 2342 is dispose on backing layer 2320 such that at least a portion of the enlarged closed end 2313 of the tubing slot abuts against the stiffening element. Stiffening element 2342 comprises a inclined branch 2342*a*, 2342*b* at each end of stiffening element 2342 that extend away from the enlarged closed end 2313 of the tubing slot such that the free ends of branches are disposed further from each other than the attached ends of the branches. Stiffening element 2342 can constrain elongation of backing layer 2320 generally within the stiffening system perimeter 2346, although elongation can occur between the free ends of the branches of stiffening element 2342.

Figure 32B:
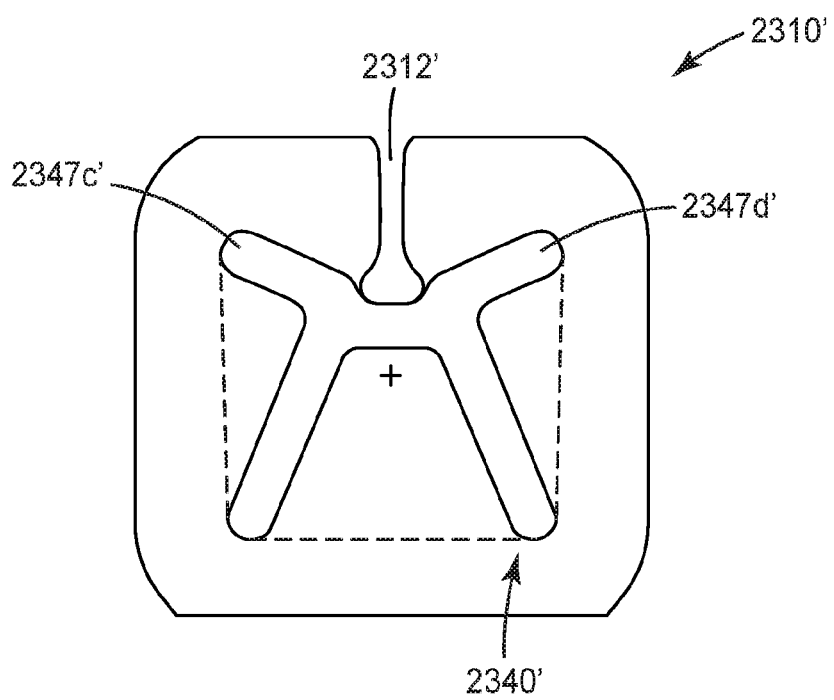

The stiffening system 2340' of medical dressing 2310' in FIG. 32B is similar to stiffening system 2340 of medical dressing 2310 of FIG. 32A, except as noted herein. Stiffening system 2340' further includes inclined secondary branches 2342*c'*, 2342*d'*, extending from stiffening element 2342 away from the enlarged closed end 2313' of the tubing slot and generally toward the top corners of the medical dressing shown in the figure (note the top edge of the figure includes the entrance to tubing slot 2312').

Figure 33:
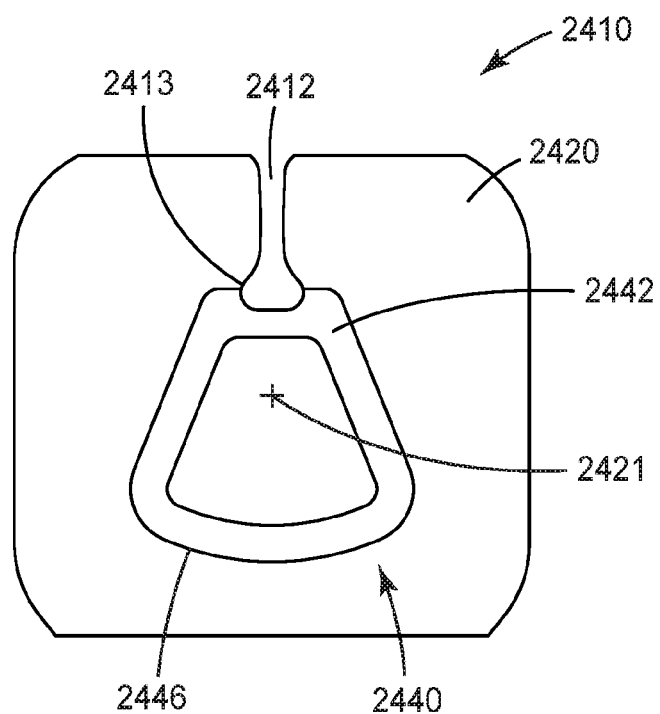
FIG. 33 depicts an embodiment of medical dressings including a stiffening system.

FIG. 33 shows another embodiment of a medical dressing 2410 having a backing layer 2420 wherein the outside edge of the backing layer defines a backing layer perimeter. A tubing slot 2412 having an enlarged closed end 2413 extends inwardly towards a geometric center 2421 of the backing layer 2420, the tubing slot 2412 aids placement of the medical dressing 2410 over a medical device to stabilize a catheter or other tubing on the skin of a patient.

Medical dressing 2410 further includes a stiffening system 2440 comprising a stiffening element 2442 to provide support to the backing layer 2420 as discussed herein with respect to other embodiments of medical dressings. The stiffening system 2440 defines a stiffening system perimeter 2446 defined by the outer edge of stiffening element 2442. Stiffening element 2442 has a closed shape disposed on backing layer 2420 around the geometric center 2421 of the backing layer such that at least a portion of the enlarged closed end 2413 of the tubing slot 2412 abuts against the stiffening element. Stiffening element 2442 can constrain elongation of backing layer 2420 generally within the stiffening system perimeter 2446.

Figure 34:
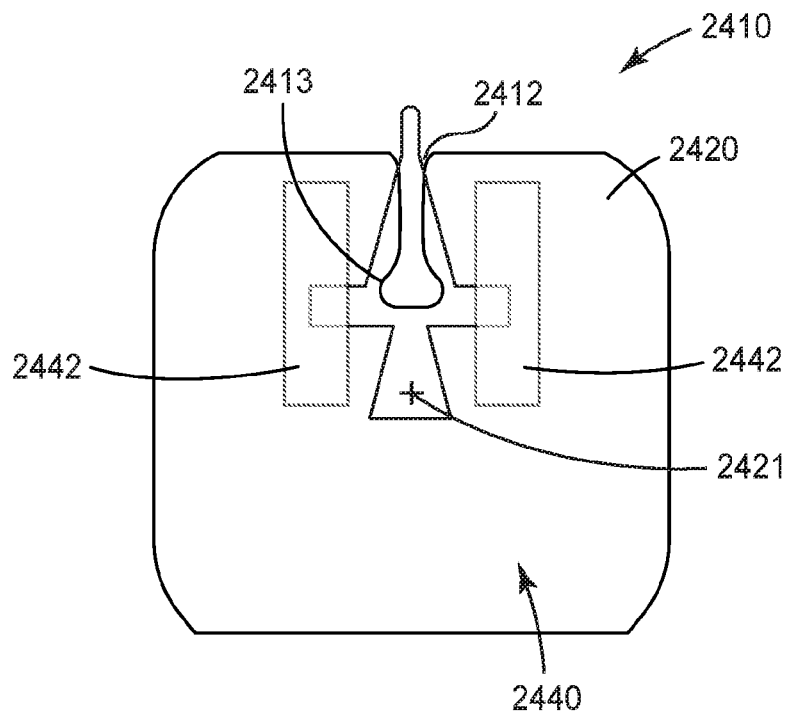
FIG. 34 depicts another embodiment of a medical dressing including a stiffening system.

FIG. 34 shows another embodiment of a medical dressing 2410 having a backing layer 2420 wherein the outside edge of the backing layer defines a backing layer perimeter. A tubing slot 2412 having an enlarged closed end 2413 extends inwardly towards a geometric center 2421 of the backing layer 2420, the tubing slot 2412 aids placement of the medical dressing 2410 over a medical device (shown here as a catheter) on the skin of a patient.

Medical dressing 2410 further includes a stiffening system 2440 comprising a stiffening element 2442 to provide support to the backing layer 2420 as discussed herein with respect to other embodiments of medical dressings. Stiffening element 2442 are rectangular in shape in either side of the tubing slot 2412 and passing over the medical device.

Potentially suitable materials, constructions, etc. of various components of one or more embodiments of the medical dressings described herein will be described generally below.

Backing Layers

The backing layers of one or more embodiments of medical dressings described herein may provide an impermeable barrier to the passage of liquids and at least some gases. Representative backing layers may include flexible polymeric films that exhibit elastomeric properties. In one or more embodiments, a transparent backing layer is desirable to allow for viewing of the underlying skin or medical device.

In one embodiment, the backing layer has high moisture vapor permeability, but is generally impermeable to liquid water so that microbes and other contaminants are sealed out from the area under the backing layer. One example of a suitable material is a high moisture vapor permeable film such as described in U.S. Pat. Nos. 3,645,835 and 4,595,001, the disclosures of which are herein incorporated by reference.

In one or more embodiments, one or more pressure-sensitive adhesives may be provided on one or both major surfaces of the backing layer to form a high moisture vapor permeable film/adhesive composite. Such composites may preferably transmit moisture vapor at a rate equal to or greater than human skin such as, for example, at a rate of at least 300 g/m$^2$/24 hrs. at 37° C./100-10% RH, or at least 700 g/m$^2$/24 hrs. at 37° C./100-10% RH, or at least 2000 g/m$^2$/24 hrs. at 37° C./100-10% RH using the inverted cup method as described in U.S. Pat. No. 4,595,001. Perforated films or pattern coated adhesives may be used to increase the moisture vapor transmission of the backing layer and/or film/adhesive composite.

In one or more embodiments, the backing layer is an elastomeric polyurethane, polyester, or polyether block amide films. These films combine the desirable properties of resiliency, elasticity, high moisture vapor permeability, and transparency. A description of this characteristic of backing layers can be found in issued U.S. Pat. Nos. 5,088,483 and 5,160,315, the disclosures of which are hereby incorporated by reference.

Commercially available examples of potentially suitable backing layers may include the thin polymeric film backings sold under the trade names TEGADERM (3M Company), OPSITE (Smith & Nephew), etc. Many other backing layers may also be used, including those commonly used in the manufacture of surgical incise drapes (e.g., incise drapes manufactured by 3M Company under the trade names STERIDRAPE and IOBAN), etc.

Because fluids may be actively removed from the sealed environments defined by one or more embodiments of the medical dressings, a relatively high moisture vapor permeable backing layer may not be required. As a result, some other potentially useful backing materials may include, for example, silicones, metallocene polyolefins, SBS block copolymer materials, SIS block copolymer materials, etc.

Regardless, however, it may be desirable that the backing layer be kept relatively thin to, e.g., improve conformability. For example, the backing layer may be formed of polymeric films with a thickness of 200 micrometers or less, or 100 micrometers or less, potentially 50 micrometers or less, or even 25 micrometers or less.

Skin-Facing Adhesives

Suitable adhesive for use in one or more embodiments of the skin-facing surfaces of medical dressings described herein include any adhesive (or combination of adhesives)

that provides acceptable adhesion to skin and is acceptable for use on skin (e.g., the adhesive should preferably be non-irritating and non-sensitizing). Suitable adhesives are pressure sensitive and in certain embodiments have a relatively high moisture vapor transmission rate to allow for moisture evaporation. Suitable pressure sensitive adhesives include those based on acrylates, urethane, hydrogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may be used in the medical dressings may include adhesives that are typically applied to the skin such as the acrylate copolymers described in U.S. Pat. No. RE 24,906, particularly a 97:3 isooctyl acrylate:acrylamide copolymer. Another example may include a 70:15:15 isooctyl acrylate:ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

Silicone adhesive can also be used. Generally, silicone adhesives can provide suitable adhesion to skin while gently removing from skin. Suitable silicone adhesives are disclosed in U.S. Pat. No. 9,359,529 (Liu et al.); U.S. Pat. No. 8,822,560 (Seth et al.); U.S. Pat. No. 8,822,559 (Zoller et al.), U.S. Pat. No. 7,407,709 (Zhou et al.), and US Patent Publication US 2011/0206924 (Liu et al.).

In one or more embodiments of medical dressings, multilayer adhesives may also be used. Some potentially useful multilayer adhesives may be described in, for example, U.S. Provisional Patent Application No. 62/785,450 titled "Multilayer Adhesive and Articles" and filed Dec. 27, 2018.

The pressure sensitive adhesives may, in some embodiments, transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as pattern coating the adhesive on the backing layer (as described in, for example, U.S. Pat. No. 4,595,001). Other potentially suitable pressure sensitive adhesives may include blown-micro-fiber (BMF) adhesives such as, for example, those described in U.S. Pat. No. 6,994,904. The pressure sensitive adhesive used in the wound dressing may also include one or more areas in which the adhesive itself includes structures such as, for example, the microreplicated structures described in U.S. Pat. No. 6,893,655.

While adhesives and adhesive articles have shown themselves to be very useful for medical applications, there are also issues in the use of adhesives and adhesive articles. Medical adhesive-related skin injury (MARSI) can have a negative impact on patient safety. Skin injury related to medical adhesive usage is a prevalent but under recognized complication that occurs across all care settings and among all age groups. In addition, treating skin damage is costly in terms of service provision, time, and additional treatments and supplies.

Medical adhesive articles such as tapes, dressings, etc. can be simply defined as a pressure-sensitive adhesive and a backing that acts as a carrier for the adhesive. The US Food and Drug Administration more specifically defines a medical adhesive tape or adhesive bandage as "a device intended for medical purposes that consists of a strip of fabric material or plastic, coated on one side with an adhesive, and may include a pad of surgical dressing without a disinfectant. The device is used to cover and protect wounds, to hold together the skin edges of a wound, to support an injured part of the body, or to secure objects to the skin."

Skin injury occurs when the superficial layers of the skin are removed along with the medical adhesive product, which not only affects skin integrity but can cause pain and the risk of infection, increase wound size, and delay healing, all of which reduce patients' quality of life. While the pathophysiology of MARSI is only partially understood, skin injury results when the skin to adhesive attachment is stronger than skin cell to skin cell attachment. When adhesive strength exceeds the strength of skin cell to skin cell interactions, cohesive failure occurs within the skin cell layer.

The intrinsic characteristics of all components of an adhesive product should be considered to address the factors that may lead to MARSI. Properties of the adhesive to be considered include cohesiveness over time and the corresponding adhesion strength; properties of the tape/backing/dressing to be considered include breathability, stretch, conformability, flexibility, and strength.

Backing Layer/Adhesive Composites

As discussed herein, the backing layers and adhesives used to secure those backing layers to the skin of a patient form a backing layer/adhesive composite. Those backing layer/adhesive composites preferably should transmit moisture vapor at a rate equal to or greater than human skin. Preferably, the adhesive coated film transmits moisture vapor at a rate of at least 300 $g/m^2/24$ hrs./37 C/100-10% RH, more preferably at least 700 $g/m^2/24$ hrs./37 C/100-10% RH, and most preferably at least 2000 $g/m^2/24$ hrs./37 C/100-10% RH using the inverted cup method as described in U.S. Pat. No. 4,595,001.

Different portions of the medical dressings described herein may include different adhesives as, for example, disclosed in US 2015/0141949 titled "Medical Dressing with Multiple Adhesives." For example, a portion of the skin-facing surface of the backing layer may include an acrylate adhesive while another portion may include a silicone adhesive. In one or more embodiments, an acrylate adhesive may be provided adjacent the perimeter, while silicone adhesive is provided near the central portion of the skin-facing surface. In one or more embodiments, an acrylate adhesive may be provided on a portion or portions of the backing layer expected to be placed over a device or tubing, while the portion or portions of the backing layer expected to contact skin are provided with silicone adhesive.

In one or more embodiments of the medical dressings described herein, the backing layer/adhesive composite may be substantially contact transparent. The term "substantially contact transparent" as used in connection with the medical dressings described herein means that, when adhered to a patient's skin, a wound, or an article (for example, a device, tubing, catheter hub, etc.), the surfaces, objects, etc. located beneath the backing layer/adhesive composite can be visually monitored (with the naked human eye) through those portions of the backing layer/adhesive composite in contact with the skin, a wound, and/or an article without requiring removal of the medical dressing. The portion or portions of the backing layer/adhesive composite that are suspended over a skin, a wound, or a device may, in one or more embodiments, also allow viewing of surfaces or objects located beneath the suspended backing layer/adhesive composite.

Stiffening System Properties and Materials

The materials used in one or more embodiments of the stiffening systems of medical dressings provide additional strength and support to the backing layer. The stiffening system material can be generally described as exhibiting more stiffness and less elasticity than the backing layer.

The stiffening system material may be used to, in one or more embodiments, form elements of a stiffening system that can be fixedly attached to backing layer. The stiffening elements of a stiffening system may be fixedly attached to one or both of the major surfaces of the backing layer. The stiffening elements of the stiffening systems described herein may be fixedly attached to the backing layer through any suitable technique or combination of techniques. Non-limiting examples of potentially suitable techniques for attaching the stiffening elements of the stiffening systems to backing layers include, but are not limited to, adhesives (for example, pressure sensitive adhesives, heat-activated laminating adhesives, etc.), glues, thermal welding, chemical welding, ultrasonic welding, etc.

While the attachment techniques described above for attaching stiffening systems to backing layers of medical dressings may be well suited for attaching stiffening systems that are provided as discrete objects to the backing layers, stiffening systems used in connection with medical dressings described herein may be formed directly on a backing layer using, for example, one or more techniques such as printing (for example, flex a graphic printing, etc.), 3D printing, casting, etc.

The phrase "attached to" (and variations thereof) as used to describe attachment of the stiffening system to a major surface of a backing layer includes both direct attachment of the stiffening elements of the stiffening system to a surface of a backing layer, as well as indirect attachment of the stiffening elements of the stiffening system to a surface of the backing layer in which one or more intervening layers, materials, etc. are located between the stiffening elements of the stiffening system and the surface of the backing layer. Non-limiting examples of potentially suitable intervening layers, materials, etc. include, but are not limited to, adhesives, foams, films, gels, release coatings, inks/colorants, primers, adhesion promoters, etc.

In one or more embodiments, it may be preferred that any such intervening layers do not significantly degrade the transfer of in-plane forces between the backing layer and the stiffening elements of the stiffening system. As used herein, "in-plane forces" are forces directed along the major surface of the backing layer to which the stiffening system is fixedly attached.

In one or more embodiments, it may be preferred that any such intervening layers do not significantly degrade the transfer of out-of-plane forces between the backing layer and the stiffening system. As used herein, "out-of-plane forces" are forces generally transverse to the major surface of the backing layer to which the stiffening system is fixedly attached.

As discussed herein with respect to the backing layer/adhesive composites provided as a part of the medical dressings described herein, the backing layer/adhesive composites may be described as being "substantially contact transparent" such that, when adhered to a patient's skin, a wound, or over an article (for example, a device, tubing, catheter hub, etc.) the surfaces, objects, etc. located beneath the backing layer/adhesive composite can be visually monitored (with the naked human eye) through those portions of the backing layer/adhesive composite in contact with the skin, a wound, and/or an article without requiring removal of the medical dressing.

The stiffening systems used in medical dressings may, in one or more embodiments, be selected based on their optical properties. For example, in one or more embodiments, the stiffening elements of stiffening systems may themselves be transparent where the term "transparent" as used herein describes an article that transmits light such that objects can be visualized through the article using the naked human eye. In one or more embodiments, a transparent article transmits at least 90% of electromagnetic radiation having wavelengths in the visible spectrum (e.g., from about 380 nm to about 740 nm).

In one or more embodiments, the stiffening elements of stiffening systems may be opaque or semi-transparent (for example, transmit light diffusely). The term "opaque" as used herein describes articles that do not allow visible light to pass through. An opaque material may be described as transmitting less than 10% of electromagnetic radiation having wavelengths in the visible spectrum (e.g., from about 380 nm to about 740 nm). The term "semi-transparent" as used herein describes articles that exhibit light transmission that is between opaque and transparent. For example, it may be possible to see blood, articles, etc. through a semi-transparent article.

Transparent, opaque, and semi-transparent articles (e.g. stiffening elements) used in stiffening systems may be colorless or may include one or more colorants such that the articles exhibit one or more selected colors when exposed to white light. In one or more embodiments, the use of one or more colors in stiffening systems may provide a visual contrast with the surrounding backing layer. The stiffening element in at least one or more embodiments can be formed from a color resin. In such embodiments, the contrast between the stiffening systems and surrounding backing layer may be useful during application of a medical dressing over a selected area, wound, article, etc. Using transparent or semi-transparent stiffening elements help maximize visibility of the skin and/or medical device disposed under the medical dressing.

One or more colored symbols may be added in the form of indicia, markings on the stiffening elements or full coloration of the stiffening elements to improve the total design form/function related aspects of the design. For example, indicia and markings may be used to aid in alignment and application of the medical dressing. In other embodiments, coloration may be used to indicate compatibility with a certain set of medical devices.

In one or more embodiments, the presence of the stiffening system elements on a backing layer may, alone, be sufficient to provide visual contrast to a medical dressing having a stiffening system located on a backing layer. In other words, visual contrast may not require the use of one or more colors. In some instances, the combination of a backing layer and stiffening element may provide a different level of light transmission as compared to the backing layer alone, and that different level of light transmission may provide some level of visual contrast that may be useful. For example, in one or more embodiments, the combination of stiffening elements and backing layer may transmit more or less light than the backing layer alone. Changes in the light transmission from the backing layer alone after application of a stiffening element may be the result of, for example, index of refraction characteristics and/or combinations that improve or reduce light transmission through the composite formed by a backing layer and stiffening element.

The stiffening systems described herein may be formed through any suitable technique or combination of techniques. Non-limiting examples of potentially suitable techniques for forming the stiffening systems include, but are not limited to, e.g., die cutting, laser cutting, water jet cutting, slitting, casting, extrusion, molding, printing, etc.

Although the embodiments of stiffening elements of stiffening systems are depicted as having flat major surfaces resulting in a generally rectangular profile when viewed in cross-sections (see, for example, FIGS. 2, 3A, 3B, and 13), it should be understood that stiffening elements used in stiffening systems described herein may have any suitable profile or shape.

In one or more embodiments, the stiffening systems described herein may be constructed of one or more materials. Non-limiting examples of potentially suitable materials that may be used to form the articles of stiffening systems described herein may include, but are not limited to, monolayer films, multilayer films, composite structures (for example, fiber-reinforced films, etc.). Suitable polymers that may be used to construct stiffening systems used in medical dressings may include, for example, Multilayer Optical Films (MOF), Biaxially Oriented Polypropylene (BOPP), simultaneously biaxially orientated PP (sBOPP), polyimide, polycarbonate, polymethylmethacrylate (PMMA), nylon, polyester, polyurethanes, Polyether Ether Ketone (PEEK), polyureas, bio-based polymers (for example, polylactic acid (PLA), etc.).

Flowable or liquid material that can be coated, extruded, printed, microreplicated or otherwise applied onto the backing to form the stiffening system. The material is cured by drying and/or crosslinking to harden and form the stiffening system. Crosslinking can be from catalyst curing or radiation curing, such as e-beam curing. Upon curing, these materials are stiffer, less elastic then the backing layer. The flowable material could be applied over substantially the entire backing and the curing could be targeted to areas of the backing. In other embodiment, the flowable material could be applied to discrete areas of the backing. Flowable material could be applied to either surface of the backing.

Optional Components

A variety of optional components may be included in one or more embodiments of medical dressings. For example, release liners may be included that covers all or a portion of any exposed adhesives to prevent contamination of those adhesives. In one embodiment, the package that contains the adhesive dressing may serve as a release liner. Suitable release liners can be made of Kraft papers, polyethylene, polypropylene, polyester or composites of any of these materials. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials.

One or more embodiments of the medical dressings described herein may include a carrier that covers all or a portion of the second major surface of the backing layer, providing structural support if the dressing is thin and highly flexible. The carrier maybe removable from the backing layer once the adhesive dressing is placed on skin. The carrier can be constructed of a variety of materials such as fabric that are woven or kitted, nonwoven material, papers, or film. In one embodiment, the carrier is located along the perimeter of the first major surface of the dressing and is removable from the first major surface, similar to the carrier used the 3M Tegaderm Transparent Film Dressing, available from 3M Company, St. Paul, Minn.

One or more embodiments of the medical dressings described herein may include an antimicrobial component that is either separate from the adhesive dressing or may be integral with the dressing. The antimicrobial component may, for example, be placed near or adjacent to, for example, an insertion site of a medical device to inhibit microbial growth in and around the insertion site, near or adjacent to a central portion of the dressing if the dressing is expected to be placed over wounds, etc. The antimicrobial component can be absorbent foam or gel, such as used in a 3M Tegaderm™ CHG I.V. Securement Dressing, available from 3M Company.

All references and publications cited herein are expressly incorporated herein by reference in their entirety into this disclosure, except to the extent they may directly contradict this disclosure. Although specific embodiments have been described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the embodiments and examples set forth herein and that such examples and embodiments are presented by way of example only with the scope of the disclosure intended to be limited only by the claims.

What is claimed is:

1. A medical dressing comprising:
 a backing layer comprising a first major surface, a second major surface, and a perimeter defining a backing area on each of the first and second major surfaces;
 adhesive on at least a portion of the first major surface of the backing layer, wherein the backing layer and the adhesive form a substantially contact transparent backing layer/adhesive composite; and
 a stiffening system fixedly attached to the backing layer, wherein the stiffening system is contained within a selected region of the backing layer, the selected region defining a region perimeter;
 wherein the stiffening system comprises a plurality of elongated stiffening elements contained within the region perimeter of the selected region, wherein each stiffening element of the plurality of stiffening elements extends along a length from a first end to a second end, wherein the first end of each stiffening element of the plurality of elongated stiffening elements is located closer to a center of the selected region than the second end, wherein the second end of each stiffening element of the plurality of elongated stiffening elements is located closer to the region perimeter than the first end, wherein each stiffening element extends across and through a central support proximate a geometric center of the stiffening system and further wherein the selected region occupied by the stiffening system is substantially contact transparent.

2. The medical dressing according to claim 1, wherein one or more of the stiffening elements of the stiffening system comprise transparent stiffening elements, and wherein the transparent stiffening elements optionally comprise a colorant such that the transparent stiffening elements exhibit a selected color when exposed to white light.

3. The medical dressing according to claim 1, wherein one or more of the stiffening elements of the stiffening system comprise opaque stiffening elements, and wherein the opaque stiffening elements optionally comprise a colorant such that the opaque stiffening elements exhibit a selected color when exposed to white light.

4. The medical dressing according to claim 1, wherein at least a portion of the region perimeter is spaced inward from the perimeter of the backing layer.

5. The medical dressing according to claim 1, wherein at least a portion of the region perimeter is coincident with the perimeter of the backing layer.

6. The medical dressing according to claim 1, wherein the region perimeter is spaced inward from the perimeter of the backing layer such that the region perimeter and the perimeter of the backing layer define a border between the region perimeter and the perimeter of the backing layer.

7. The medical dressing according to claim 1, wherein the selected region is centered on the backing layer.

8. The medical dressing according to claim 1, wherein the second end of each stiffening element of the plurality of elongated stiffening elements is spaced inward from the perimeter of the backing layer and is completely surrounded by the backing layer.

9. The medical dressing according to claim 1, wherein the backing layer comprises a geometric center and wherein the selected region comprises a geometric center, and further wherein the geometric center of the backing layer and the geometric center of the selected region are coincident with each other.

10. The medical dressing according to claim 1, wherein the backing layer comprises a geometric center and wherein the selected region comprises a geometric center, and further wherein the geometric center of the backing layer and the geometric center of the selected region are offset from each other.

11. The medical dressing according to claim 1, wherein a width of two or more stiffening elements of the the plurality of elongated stiffening elements are uniform along the length of the stiffening element.

12. The medical dressing according to claim 1, wherein the second ends of the plurality of elongated stiffening elements define a stiffening system perimeter, wherein a geometric center of the backing layer is located within the stiffening system perimeter.

13. The medical dressing according to claim 1, wherein the selected region occupies 50% or more of the backing area.

14. The medical dressing according to claim 1, wherein the stiffening system occupies 50% or less of the selected region.

15. The medical dressing according to claim 1, wherein the second ends of two or more stiffening elements of the plurality of elongated stiffening elements extend to the perimeter of the backing layer.

16. The medical dressing according to claim 1, wherein the second ends of all stiffening elements of the plurality of elongated stiffening elements are spaced inward from the perimeter of the backing layer such that the second ends of all stiffening elements of the plurality of elongated stiffening elements are surrounded by the backing layer.

17. The medical dressing according to claim 1, wherein the first ends of two or more stiffening elements of the plurality of elongated stiffening elements are attached to each other.

18. The medical dressing according to claim 1, wherein the stiffening system comprises a central support proximate the geometric center, wherein the first ends of two or more stiffening elements of the plurality of elongated stiffening elements are attached to the central support.

\* \* \* \* \*